United States Patent [19]

Gagnon

[11] Patent Number: 5,443,727
[45] Date of Patent: Aug. 22, 1995

[54] ARTICLES HAVING A POLYMERIC SHELL AND METHOD FOR PREPARING SAME

[75] Inventor: David R. Gagnon, St. Paul, Minn.

[73] Assignee: Minnesota Mining and Manufacturing Company, St. Paul, Minn.

[21] Appl. No.: 122,807

[22] Filed: Sep. 16, 1993

Related U.S. Application Data

[63] Continuation of Ser. No. 775,969, Nov. 8, 1991, abandoned, which is a continuation-in-part of Ser. No. 605,834, Oct. 30, 1990, abandoned, Ser. No. 605,754, Oct. 30, 1990, abandoned, Ser. No. 605,948, Oct. 30, 1990, abandoned, Ser. No. 605,921, Oct. 30, 1990, abandoned, Ser. No. 605,828, Oct. 30, 1990, abandoned, and Ser. No. 605,757, Oct. 30, 1990, abandoned.

[51] Int. Cl.$^6$ .............................................. B01D 71/38
[52] U.S. Cl. ................................. 210/490; 210/500.42
[58] Field of Search ................... 210/500.42, 654, 490; 427/245, 52, 54

[56] References Cited

U.S. PATENT DOCUMENTS

| | | | |
|---|---|---|---|
| 2,765,233 | 10/1956 | Sarett et al. | 99/178 |
| 3,853,601 | 12/1974 | Taskier | 117/98 |
| 3,892,575 | 7/1975 | Watts et al. | 427/54 X |
| 3,941,718 | 3/1976 | Barabas et al. | 252/430 |
| 4,143,218 | 3/1979 | Adams et al. | 429/254 |
| 4,192,773 | 3/1980 | Yoshikawa et al. | 525/429 |
| 4,197,181 | 4/1980 | Portal et al. | 204/283 |
| 4,298,666 | 11/1981 | Taskier | 429/206 |
| 4,301,195 | 11/1981 | Mercer et al. | 427/261 |
| 4,302,334 | 11/1981 | Jakabhazy et al. | 210/500.2 |
| 4,328,076 | 4/1982 | Fisher et al. | 204/14 R |

(List continued on next page.)

FOREIGN PATENT DOCUMENTS

| | | |
|---|---|---|
| 0203459 | 5/1986 | European Pat. Off. . |
| 0272923 | 6/1988 | European Pat. Off. . |
| 0359925 | 7/1989 | European Pat. Off. . |
| 0370657 | 11/1989 | European Pat. Off. . |
| 2817854 | 1/1979 | Germany . |
| 50-139184 | 6/1975 | Japan . |
| 62-14903 | 1/1987 | Japan . |
| 62-277106 | 12/1987 | Japan . |
| 1601529 | 10/1981 | United Kingdom . |

OTHER PUBLICATIONS

Harris, *J. Polymer Sci.*, Part A-1, vol. 4, 665-677 (1965).
Haas et al., *J. Polymer Sci.*, vol. 22, 291-302 (1956).
Ikada et al., "Blood Compatibility of Hydrophilic Polymers,", *J. Biomedical Materials Research*, 15:697-718 (1981).

(List continued on next page.)

*Primary Examiner*—Frank Spear
*Attorney, Agent, or Firm*—Gary L. Griswold; Walter N. Kirn; John H. Hornickel

[57] ABSTRACT

Articles having a complex geometric configuration have hydrophilicity imparted to at least a portion of surfaces of the articles while substantially retaining the complex geometric configuration. The hydrophilicity is imparted by an extremely thin, self-interlocking shell of tactic, hydrophilic poly(vinyl alcohol) enveloping the surfaces. A tactic poly(vinyl alcohol) precursor applied to surfaces of the supporting structure is reacted in situ on the surfaces with a hydrolysis reagent to prepare the tactic, hydrophilic poly(vinyl alcohol) shell. The article having the hydrophilic shell is highly resistant to solvent washout. Hydrophilicity and hydrophobicity can be reversibly provided on regio-specific surfaces of the article. Articles in the form of membranes useful as filters, residue barriers for electroplating devices, separators for electrochemical cells, and drug delivery device components are also described. Membranes to form permanent and undistorted images, and methods of preparing such images from image-forming substances in receptive media are also provided. Hydrophilic porous supporting structures loaded with an enzyme system which catalyzes a reaction of a substrate, oxygen, and if necessary, water or moisture to consume oxygen are also described for oxygen scavenging in packages containing oxygen sensitive products.

30 Claims, 6 Drawing Sheets

$1\,\mu m$

U.S. PATENT DOCUMENTS

| Patent No. | Date | Inventor | Class |
|---|---|---|---|
| 4,342,635 | 8/1982 | Becker et al. | 204/263 |
| 4,346,142 | 8/1982 | Lazear | 428/315.7 |
| 4,354,308 | 10/1982 | Shimada et al. | 29/571 |
| 4,394,457 | 7/1983 | Ogasa | 521/54 |
| 4,438,185 | 3/1984 | Taskier | 429/250 |
| 4,440,830 | 4/1984 | Wempe | 428/352 |
| 4,501,793 | 2/1985 | Sarada | 428/315.5 |
| 4,524,015 | 6/1985 | Takahashi et al. | 252/188.28 |
| 4,528,325 | 7/1985 | Ofstead | 252/60 |
| 4,615,784 | 10/1986 | Stewart et al. | 204/263 |
| 4,618,649 | 10/1986 | Ofstead | 525/60 |
| 4,640,865 | 2/1987 | Lancaster et al. | 428/421 |
| 4,675,213 | 6/1987 | Yamamori et al. | 427/244 |
| 4,687,481 | 8/1987 | Nuwayser | 604/897 |
| 4,693,939 | 9/1987 | Ofstead | 428/421 |
| 4,694,037 | 9/1987 | Ofstead | 524/557 |
| 4,749,487 | 6/1988 | Lefebvre | 210/490 |
| 4,753,725 | 6/1988 | Linder et al. | 210/654 |
| 4,776,959 | 10/1988 | Kasai et al. | 210/490 |
| 4,778,596 | 10/1988 | Linder et al. | 210/638 |
| 4,780,514 | 10/1988 | Ofstead | 526/245 |
| 4,794,002 | 12/1988 | Henis et al. | 424/488 |
| 4,840,992 | 6/1989 | Ofstead | 525/61 |
| 4,849,224 | 7/1989 | Chang et al. | 424/434 |
| 4,849,457 | 7/1989 | Ichii et al. | 521/62 |
| 4,861,644 | 8/1989 | Young et al. | 428/195 |
| 4,878,212 | 10/1989 | Kuder | 369/100 |
| 4,885,086 | 12/1989 | Miura | 210/321.8 |
| 4,894,253 | 1/1990 | Heineman et al. | 427/36 |
| 4,911,844 | 3/1990 | Linder et al. | 210/638 |
| 4,917,895 | 4/1990 | Lee et al. | 424/448 |
| 4,921,884 | 5/1990 | Hammer et al. | 523/106 |
| 4,921,908 | 5/1990 | Ofstead | 525/61 |
| 4,943,373 | 7/1990 | Onishi et al. | 210/500.42 |
| 4,943,374 | 7/1990 | Heininger et al. | 210/651 |
| 4,944,879 | 7/1990 | Steuck | 210/500.27 |
| 4,963,494 | 10/1990 | Hibino et al. | 435/288 |
| 5,006,216 | 4/1991 | Dietrich et al. | 204/257 |
| 5,037,656 | 8/1991 | Pitt et al. | 424/443 |
| 5,041,225 | 8/1991 | Norman | 210/500.36 |
| 5,049,275 | 9/1991 | Gillberg-LaForce et al. | 210/500.27 |

OTHER PUBLICATIONS

Sato et al., "Study on Interactions Between Plasma Proteins and Polymer Surface", *Polymer Journal*, 16: No. 1 pp. 1–8 (1984).

Saito, "On Food Quality Preservation By Means of Free Oxygen Absorber", *Journal Yukaqaku*, 28, No. 1, pp. 45–54 (1979) (Translated with pagination 1–23).

Labuza et al., "Applications of Active Packaging for Improvement of Shelf Life and Nutritional Quality of CAP/MAP Foods", *J. Food Processing and Preservation*, 13:1–69 (1989).

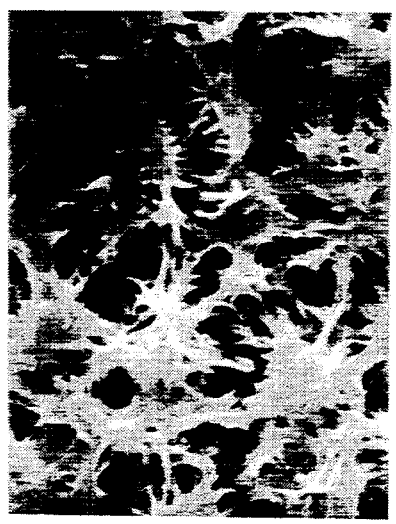 
1 μm
Fig. 1a
1 μm
Fig. 1b

/μm    /μm

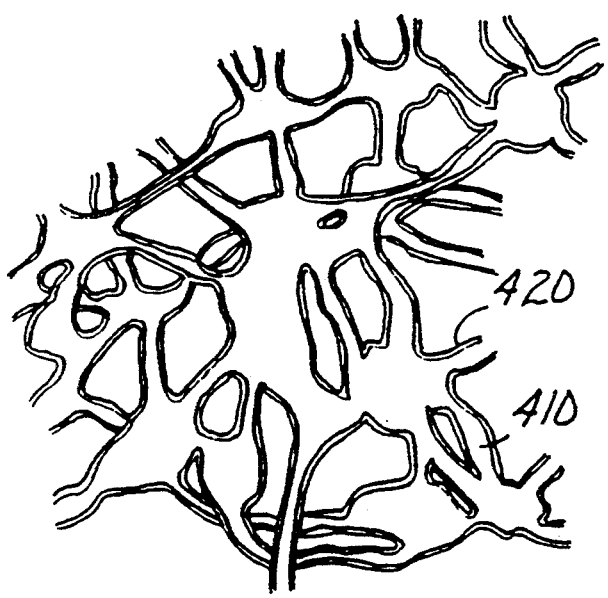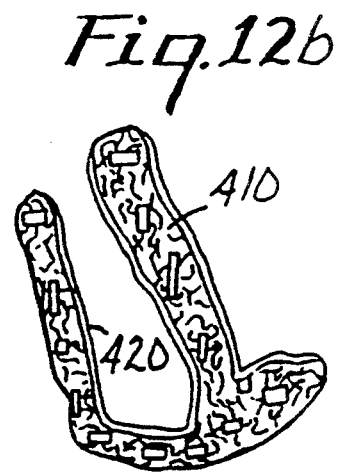
Fig. 12a
Fig. 12b

ARTICLES HAVING A POLYMERIC SHELL AND METHOD FOR PREPARING SAME

This is a continuation of application No. 07/775,969 filed Nov. 8, 1991, now abandoned, which is a continuation-in-part of applications Nos. 07/605,834, filed Oct. 30, 1990; 07/605,754, filed Oct. 30, 1990; 07/605,948, filed Oct. 30, 1990; 07/605,921, filed Oct. 30, 1990; 07/605,828, filed Oct. 30, 1990; and 07/605,757, filed Oct. 30, 1990; all now abandoned.

FIELD OF THE INVENTION

This invention relates to articles such as membranes having an extremely thin hydrophilic polymeric shell about surfaces of the article while substantially retaining the geometric configuration of the article, the use of hydrophilic microporous membranes in separation, drug delivery, image forming, oxygen scavenging and other purification processes, and the method of preparing such articles.

BACKGROUND OF THE INVENTION

Many polymeric materials are hydrophobic. When such materials are formed into films, beads, membranes or the like, their hydrophobic nature prevents or inhibits "wetting" by water.

When used to describe a surface, the term "hydrophobic" means that water on that surface has a contact angle of greater than ninety degrees. By contrast, the term "hydrophilic" applies to those polymeric surfaces which have a contact angle of less than ninety degrees.

While hydrophobic materials are well known in the art and easily prepared, their usefulness in many processes and products is severely restricted by their hydrophobicity. There have been numerous prior attempts to render a hydrophobic material hydrophilic in order to be useful in processes where water is present and must "wet" the surface of the material.

Several efforts have concentrated in rendering hydrophilic a porous hydrophobic polymeric membrane. Despite the low cost of preparation of such hydrophobic materials in the form of porous membranes, such membranes are not useful as membranes in aqueous systems because capillary forces at the pores of such hydrophobic materials prevent the wetting of the pores by water, aqueous solutions, or other high surface tension organic solutions.

Treatment of the surfaces of hydrophobic materials, such as porous membranes, made from polyolefins has been attempted using surfactant coatings such as the silicone glycol copolymer disclosed in U.S. Pat. No. 3,853,601 (Taskier) or the nonionic alkylphenoxy poly(ethyleneoxy)ethanol surfactant disclosed in U.S. Pat. No. 4,501,793 (Sarada), or a copolymer coating having hydrophilic monomeric units and hydrophobic monomeric units such as an ethylene-vinyl alcohol copolymer disclosed in European Patent Office Publication No. 0 023 459 (Nitadori et al.). Unfortunately, such surfactant treatments to the surfaces of hydrophobic materials may not be permanent due to the washing away of such surface coatings by water or a variety of organic solvents including those used to form the coating on the supporting hydrophobic article. Also, surfactants are commonly known to denature enzymes. See, for example, Molecular Cell Biology, J. Darnell et al. Fds., Scientific American Books, 232, (1986).

Another approach taken in the art is the adsorption of a hydrophilic polymer on a hydrophobic substrate, as disclosed in U.S. Pat. No. 4,794,002 and corresponding European Patent Office Publication 0 221 046 (Henis et al.). A modifying polymer may be adsorbed onto the surfaces of a polysulfone or a polyethersulfone from an aqueous solution of the modifying polymer. But the modifying polymer can be removed with detergent solutions and the like.

Relatively permanent hydrophilic coatings on hydrophobic microporous films have been attempted by further treatment of chemical cross-linking of or ionizing radiation directed against the coating. U.S. Pat. No. 4,346,142 (Lazear) discloses an ionizing radiation process. U.S. Pat. No. 4,776,959 (Kasai et al.) discloses thermally curing a water insoluble vinyl alcohol-vinyl acetate copolymer onto a porous membrane. U.S. Pat. No. 4,753,725 (Linder et al.) discloses semipermeable composite membranes made by reacting PVA/PVA-copolymer films with a monomeric organic compound containing at least two functional groups, a linear or branched polyfunctional oligomer or polymer, and a compound containing cross-linking and ionizable groups. Japanese Publ. No. JP62-14903 (Ohtani et al.) describes using a solution containing a compound having ester side chains and a crosslinking agent to thermally crosslink the ester side chains to hydroxyl or carboxyl reactive sites on the hydrophobic polymer.

Others have attempted to apply hydrophilic poly(vinyl alcohol) directly to the hydrophobic polymer membrane. Japanese Publ. No. JP62-277106 (Ikehara et al.) describes the ionic cross-linking of a poly(vinyl alcohol) on a microporous polymer substrate from a water-soluble poly(vinyl alcohol) polymer containing an inorganic alkaline compound. While poly(vinyl alcohol) has excellent hydrophilicity, processing difficulties are encountered when one attempts to coat hydrophilic poly(vinyl alcohol) directly onto the hydrophobic membrane from a polar or aqueous solution.

Another has attempted to form hollow fiber microporous membranes with poly(vinyl alcohol) chemically bonded to the surfaces of the hollow fiber membrane. U.S. Pat. No. 4,885,086 (Miura) discloses that a hollow fiber membrane is irradiated with ionizing radiations and then reacted with vinyl acetate and hydrolyzed.

The attempts described in the art to provide a hydrophilic poly(vinyl alcohol) coating are based on using atactic poly(vinyl alcohol), which has a low crystallinity content. It is believed that coatings based on atactic poly(vinyl alcohol) are more soluble in a range of solvents and aqueous fluids and consequently the coatings are more readily washed away, particularly when contacted with solvents miscible with the solvents used to bring the hydrophilic material in contact with the hydrophobic membrane.

It is possible to produce poly(vinyl alcohol) which is not atactic. Preparation and the properties of syndiotactic and isotactic poly(vinyl alcohol) have been described in Harris et al., Journal of Polymer Science: Part A-1, Vol. 4, 665–677 (1966), describing the preparation of syndiotactic poly(vinyl alcohol) from poly(vinyl trifluoroacetate) and isotactic poly(vinyl alcohol) from poly(vinyl tert-butyl ether). Further, the production of poly(vinyl trifluoroacetate) as a precursor for syndiotactic poly(vinyl alcohol) has been described in Haas et al., Journal of Polymer Science, Vol. 22, pgs. 291–302 (1956).

Prior uses of such tactic poly(vinyl alcohol) materials have included the preparation of ophthalmic articles, such as contact lenses and coatings for such articles, from non-crosslinked poly(vinyl alcohol) copolymers hydrated to have controlled hydrogel properties and high strength. Co-assigned, related U.S. Pat. Nos. 4,528,325; 4,618,649; 4,693,939; 4,694,037; 4,780,514; 4,840,992; and 4,921,908 (Ofstead) disclose these copolymers and shaped articles, with U.S. Pat. No. 4,693,939 disclosing these copolymers as coatings on articles.

Non-crosslinked crystallized poly(vinyl alcohol) coatings have been disclosed for use with a variety of medical devices. European Patent Publication 0 370 657 (Ofstead) discloses a poly(vinyl alcohol) coating on medical devices (such as catheter guidewires), which is prepared by coating atactic poly(vinyl alcohol) on the device and then annealing the coating to crystallize the poly(vinyl alcohol) to provide a slippery surface.

However, the art of preparing crystallized poly(vinyl alcohol) hydrogel coatings has failed to recognize that in many instances it is desirable to retain the particular geometric configuration of the article being coated. Crystallized poly(vinyl alcohol) which is capable of becoming a hydrogel in the presence of water can disrupt a complex geometric configuration of a supporting structure, such as by blocking the pores of a microporous membrane, if the coating applied to the supporting structure is not carefully controlled.

Filters

The use of porous membrane materials in purification and separation processes is well known. While these porous membrane materials exhibit excellent efficiency in removing fine particulate materials from a fluid, reasonable flow rates of filtrate through the membrane generally require a close match between the polarity of the fluid and the surface energy of the material used to prepare the membrane.

A wide range of materials, including both hydrophobic and hydrophilic materials, have been used to prepare semipermeable membranes. Often, membranes based on hydrophobic materials are stronger than membranes based on hydrophilic membranes, allowing the hydrophobic membranes to be subjected to higher pressures than hydrophilic membranes as a means of improving flow rates through the filter.

The use of porous membrane filters in applications involving aqueous fluids is increasing, as is the need for hydrophilic porous membranes having physical properties comparable to those realized with many hydrophobic membranes.

Prior attempts to produce hydrophobic membranes having hydrophilic surfaces have generally been unsuccessful, leading to non-permanent treatments, treatments which affected only the outer surface of the membrane and not the surfaces of the inner pores, or treatments which occluded or significantly reduced the pore size of the membrane.

Electroplating Devices

Electroplating devices require residue barriers to contain particulates generated during the electroplating process and other debris in order to maintain the quality of the electrodeposit of metal on a substrate. A residue barrier must not interfere with the transfer of metallic ions or otherwise provide any resistance to the plating current flow.

Electroplating solutions are generally aqueous solutions. A residue barrier must be hydrophilic and porous in order for the metallic ions in an agitated solution to pass through the barrier while the debris is blocked from passage. Hydrophobic microporous membranes would be excellent residue barriers if only such membranes were hydrophilic.

Electrochemical Cell Separators

Microporous membrane materials are frequently utilized as separator materials for electrochemical cells wherein they provide a physical barrier between the cell electrodes, keeping plates of opposite polarity from coming into direct contact with each other. In addition to having dimensional stability sufficient to maintain a physical barrier, the membrane material must also be non-conductive. The membrane material also must be porous so that cell electrolyte can pass through the separator to provide an internal conducting path between electrodes. Notwithstanding the need for porosity, the membrane material must minimize penetration through the separator of particulate matter either arising from flaking or colloidal dispersion of electrode materials or arising from dendrite formation during charging. The membrane material must also be chemically inert to the environment established by the cell.

Preferably, the separator is in the form of a microporous membrane having a high void volume which permits substantially unimpeded transport of electrolyte through the separator while exhibiting good dendristatic properties.

Transdermal Drug Delivery Devices

Transdermal drug delivery devices provide an advantageous means for delivering many therapeutic agents. The use of such devices avoids "first pass" metabolism by the liver, increases patient compliance, and provides sustained delivery of the agent.

Some of the devices employ a microporous membrane to control the rate at which the therapeutic agent is delivered from the device to the skin. Other devices employ a microporous membrane to isolate the therapeutic agent in a reservoir.

However, the microporous membranes currently employed are hydrophobic. This hydrophobicity severely limits the utility of the membranes for use in transdermal delivery devices with a therapeutic agent which is hydrophilic. A hydrophobic membrane would block delivery of a hydrophilic therapeutic agent and would not release a therapeutic agent from isolation in a reservoir at the desired rate.

Hydrophobic microporous membranes would have broader utility in drug delivery devices for the controlled delivery of hydrophilic therapeutic agents if the membranes could be rendered hydrophilic while still retaining the geometric configuration of the membrane.

Plastic Sheets

The production of a plastic sheet having a porous surface is disclosed in U.S. Pat. No. 4,849,457 (Ichii et al.). The plastic sheet of a combination of polyester and polyurethane, acrylonitrile-styrene copolymer and cellulose acetate, and either polyvinyl chloride homopolymer or copolymer and either polyacrylonitrile homopolymer or copolymer has high porosity and absorbability, which is useful in the printing of characters and images. The plastic sheet may serve as a transfer sheet in a heat-melting type thermal-transfer printing apparatus.

Another method of preparing plastic sheets for transparency films is disclosed in U.S. Pat. No. 4,301,195 (Mercer et al.). The method involves coating a polyester or cellulose transparency film with a water-swellable hydrophilic polymer. To minimize smudging of ink or the transfer of ink to a contacting surface, a second coating containing starch particles is often put onto the surface, which may result in a "grainy" image. Also moisture from fingerprints may mar the image by affecting the water swellable hydrophilic polymer coating. Often, a transparent sleeve is employed to protect the imaged transparency from contact with moisture.

Oxygen Scavengers

Certain food products are subject to deterioration upon exposure to atmospheric oxygen during storage. Previous methods of preserving such materials have included: freezer storage, (which is not practical for many foodstuffs); vacuum packaging, (which is not practical for fragile foods); gas-flushing the package with an inert gas prior to sealing the package (which is largely ineffective due to package oxygen permeability); and more recently, the use of oxygen-reactive materials as scavengers. A survey of oxygen scavengers such as inorganic dithionite salts, specially processed iron powders, and sugar-based alkali denatured products used to preserve the quality of food is described in Saito, "On Food Quality Preservation By Means of Free Oxygen Absorber," Journal Yukagaku, 28, No. 1 (1979), pp 1–23. Oxygen scavenging systems are also described in Labuza et al., "Applications of Active Packaging for Improvement of Shelf Life and Nutritional Quality of CAP/MAP Foods", J. Food Processing and Preservation, 13: 1–69; 1989.

The specially processed iron powders are often packaged in gas-permeable pouches and added to he package containing the food product. See, for example, the disclosures of U.S. Pat. Nos. 4,192,773 (Yoshikawa et al.) and 4,524,015 (Takahashi et al.). But these sachets added to food packaging complicate the food processing automated operations and are not generally favored by consumers.

An enzyme treated fabric sheet for wrapping a moist food product is disclosed in U.S. Pat. No. 2,765,233 (Sarett et al.). The enzyme system on the surface of the sheet will be in contact with the article being wrapped and is preferably in a water dispersible binder. If the article does not contain glucose, the sheet may be coated or impregnated with glucose along with the enzyme system. The system relies on a two step oxidation reaction of glucose, glucose oxidase, oxygen, and water found at the interface between the moist food product and the outer surface of the wrapping sheet.

Likewise, Japanese patent publication JP 75/139184 (Okada et al.) describes a food packaging film thickly coated with enzymes and glucose in a water soluble binder.

SUMMARY OF THE INVENTION

The present invention describes a supporting structure having a complex geometric configuration and an extremely thin hydrophilic polymer shell which imparts hydrophilicity to the structure. The present invention also describes a method of providing such hydrophilicity while substantially retaining the geometric configuration of the structure.

The present invention also provides a hydrophilic membrane for electroplating residue barriers which traps debris but does not substantially impair electroplating current. The residue barrier of the present invention, either surrounding an anode or positioned between an anode and an cathode of an electroplating device, does not appreciably interrupt the current flow or metallic ion transport vital to an electroplating process while blocking residue and debris harmful to the electroplating process.

The present invention also provides a hydrophilic microporous electrochemical cell separator material as a residue barrier for particulates and debris yet permits substantially unimpeded transport of electrolyte through the separator.

The present invention also provides a hydrophilic microporous drug delivery membrane having an extremely thin hydrophilic polymer shell which imparts hydrophilicity to the microporous membrane without otherwise substantially altering the membrane.

The present invention also provides a microporous hydrophilic membrane filter, suitable for separating solids from fluids.

The invention overcomes the deficiencies in the prior art by providing a supporting structure having a complex geometric configuration enveloped at at least a portion of its surfaces by an extremely thin, self-interlocking shell of tactic, hydrophilic homopolymer or copolymer of poly(vinyl alcohol) while substantially retaining the complex geometric configuration of the supporting structure. The tactic poly(vinyl alcohol) shell may be either syndiotactic or isotactic.

As used herein, "complex geometric configuration" refers to the multiplicity and types of surfaces of a supporting structure when observed on a micron scale. The extremely thin shell of poly(vinyl alcohol) on a supporting structure envelops the multiplicity of such surfaces without altering the type of such surfaces. Thus, the poly(vinyl alcohol) shell imparts hydrophilicity to a supporting structure while substantially retaining the complex geometric configuration of the supporting structure.

The multiplicity of surfaces of a supporting structure are enveloped by the poly(vinyl alcohol) shell. "Envelop" means the shell entirely surrounds each of the multiple surfaces and imparts hydrophilicity thereto. Integrity is imparted by the formation of crystalline crosslinks within the shell., i.e., the formation of tie molecules connecting two or more crystallites. Thus, the shell is self-interlocking mechanically about the surfaces of the supporting structure without substantial covalent, ionic, or van der Waals interaction with such surfaces.

The type of surfaces that a supporting structure may have may be expressed in terms of Euclidean geometry, fractal geometry, or a combination of both.

A fractal is an object or process that cannot be represented by Euclidean geometry. With the complexity of natural shapes and surfaces being so jagged that they have more than two dimensions, fractal geometry has become useful to analyze shapes so commonly found in nature. (Van Nostrand's Scientific Encyclopedia Seventh Edition, Van Nostrand Reinhold 1989, p. 1221.)

Euclidean surfaces may be planar, curved, or any other topography which may exhibit a Euclidean geometric configuration.

Fractal surfaces may be porous, tentacular, jagged, uneven, undulating, irregular, asymmetrical, or of any other topography which may exhibit a non-Euclidean geometric configuration.

For example, a porous membrane or bead may appear to have surfaces which are planar or spherical, respectively, i.e., in a Euclidean geometric configuration. But at a micron scale, the membrane and bead have a complex geometric configuration, because a precise examination of the multiplicity of surfaces shows a fractal, three dimensional terrain which defies Euclidean characterization. The pores of the membrane or bead are uneven, irregular, and unpatterned in all of the three dimensions Euclidean geometry measures. The fractal surfaces surrounding such pores generate a complex geometric configuration for the supporting fractal structure. The poly(vinyl alcohol) shell of the present invention envelops such fractal surfaces defining such pores but does not cover or fill such pores or otherwise convert the fractal configuration of the surfaces to a Euclidean configuration.

In another example, a non-woven web may appear to be flat and have a Euclidean geometric configuration. But at a micron scale, surfaces of the web are an unpatterned layering of strands which give the non-woven web a complex geometric configuration, even if the individual strands comprising the web have a Euclidean geometric configuration. The poly(vinyl alcohol) shell of the present invention envelops the strands of the web while substantially retaining the complexity of the surfaces and the fractal configuration of the non woven web.

The hydrophilic, polymeric shell enveloping the supporting structure is "extremely thin", on a scale of monolayers of polymer. "Extremely thin" means that the shell's monolayer dimension is such that it does not substantially clog, smooth, block, or swell in manner to appreciably alter a supporting structure's complex geometry. Unlike a hydrogel coating, which, upon exposure to water would swell and significantly alter a geometric configuration of a supporting structure, the self-interlocking shell of poly(vinyl alcohol) of the articles of the present invention does not appreciably swell, substantially retaining the complex geometry of the article.

A supporting structure such as a membrane may have a Bubble Point Pore Size (c.f. ASTM F-316) of about 0.01 to 20 $\mu$m. The present invention finds that an extremely thin shell of hydrophilic polymer having less than about an average of 100 Angstroms thickness forming a shell on fractal surfaces of the membrane reduces the effective pore size less than about 30 percent and desirably less than about 15 percent. The complex geometric configuration of the supporting structure is substantially retained.

Thus, the present invention allows the supporting structure to acquire a hydrophilic surface without altering its physical configuration.

The supporting structure has at least one surface in a complex geometric configuration which the poly(vinyl alcohol) shell may envelop. Nonlimiting examples of a supporting structure include films, porous membranes, beads, woven and non-woven webs, spun threads, hollow porous fibers, and porous fibers. Nonlimiting examples of the composition of the supporting structure may be polymeric, ceramic, cellulosic, glassy, metallic, or carbonaceous.

A polymeric structure may be made from any useful and formable polymeric material which does not dissolve substantially in the presence of solvents used with precursors to make the shell. Nonlimiting examples include without limitation, polyolefins (e.g., polyethylene and polypropylene), polyhalo olefins (e.g., polytetrafluoroethylene and polyvinylidene fluoride), nylon, polyesters (e.g., polyethylene terephthalate), polysulfones, polyethersulfones, poly(2,6-dimethyl,4-phenylene oxide) and derivatives thereof, polyamides, polyimides, polyetherimides, or polymeric materials previously unavailable for forming hydrophilic polymeric structures.

The tactic, hydrophilic shell of a homopolymer or copolymer of poly(vinyl alcohol) is formed in-situ about complex, envelopable surfaces of the supporting structure by hydrolysis (e.g., alcoholysis or ammonolysis) of a tactic hydrophobic polymeric poly(vinyl alcohol) precursor with a hydrolysis reagent.

"Hydrolysis" means the cleaving of an ester or ether group in the presence of a hydrolysis reagent to form an alcohol group.

The hydrophobic polymeric poly(vinyl alcohol) precursor can be any tactic poly(vinyl alcohol) precursor which forms a tactic homopolymer or copolymer of poly(vinyl alcohol), including without limitation, homopolymers of vinyltrifluoroacetate and copolymers of vinyltrifluoroacetate monomers and monomers having a vinylic group therein, homopolymers of vinyl tert-butyl ether monomers, and copolymers of vinyl tert-butyl ether monomers and monomers having a vinylic group therein. For purposes of describing this invention, references to poly(vinyl alcohol) shall include both a homopolymer of poly(vinyl alcohol) and a copolymer of vinyl alcohol and another co-monomer.

The invention also overcomes problems confronted in the prior art by providing a method for generating an extremely thin shell of tactic poly(vinyl alcohol) about envelopable surface(s) of a supporting structure. The method employs applying a tactic, polymeric poly(vinyl alcohol) precursor to surfaces of the supporting structure, and then causing, in-situ, a hydrolysis reaction to form a tactic, hydrophilic poly(vinyl alcohol) shell enveloping such surfaces while retaining the complex geometric configuration of the supporting structure.

The hydrolysis reagent may be a reagent which causes the formation of tactic poly(vinyl alcohol), whether such reaction occurs in liquid or gaseous phase. Preferably, the hydrolysis reagent is a basic reagent having a pH greater than about 7.0. Suitable reagents include, but are not limited to, dissolved or anhydrous ammonia, sodium hydroxide, sodium carbonate, and potassium hydroxide.

Many desirable articles having a hydrophilic polymeric shell thereon may be made and used in accordance with the present invention. The article may take the form of porous membranes where fractal surfaces define pores and interstices in and through the membrane. The shell of poly(vinyl alcohol) does not substantially alter the complex geometric configuration of the membrane. Such membranes may be used to separate particles in a flowing medium.

Many desirable electroplating residue barriers may be made and used in accordance with the present invention. Particularly, a hydrophilic, microporous membrane of the present invention may be used as an anode bag surrounding the anode of an electroplating device. Alternatively, a hydrophilic, porous membrane of the present invention may be used as an electroplating diaphragm separating the cathode and anode compartments with positive pressure electrolyte solution flow through the compartments. Preferably, the diaphragm membrane may be microporous to restrict the movement of micron-sized particles regardless of electrolyte solution flow characteristics.

The present invention further provides a hydrophilic microporous membrane material suitable for use as a separator for an electrochemical cell. The hydrophilic membrane material is substantially non-conductive, chemically inert to the electrochemical cell environment, and provides a residue barrier while having sufficient porosity to allow the cell's electrolyte to pass substantially unimpeded through the membrane. An electrochemical cell separator residue barrier, positioned between an anode and a cathode of an electrochemical cell minimizes movement of electrode debris originating from flaking, colloidal dispersion, or dendrite formation.

A microporous membrane may be used as a layer in a drug delivery device for controlling the rate of delivery of a therapeutic agent through the device and to the skin of a patient or for isolating the therapeutic agent in a reservoir until use commences. Thus, the invention also provides a drug delivery device comprising a hypoallergenic pressure sensitive adhesive layer, a therapeutic active agent and the hydrophilic microporous membrane contacting the adhesive layer and in communication with the therapeutic agent. The drug delivery device may employ the hydrophilic membrane between the skin and a reservoir containing the therapeutic agent or may employ the membrane as a depot for a therapeutic agent.

The present invention provides a hydrophilic polymeric self-interlocking shell about surfaces of a supporting structure while substantially retaining the complex geometric configuration of the structure, and to permit that hydrophilized article to be used in aqueous systems or with organic solvents without adversely affecting the hydrophilic polymeric shell.

The present invention also provides a method for forming an extremely thin shell of tactic, hydrophilic poly(vinyl alcohol) about a supporting structure, such as a microporous membrane, through the use of a tactic poly(vinyl alcohol) precursor capable of being converted, in-situ, on at least a portion of the complex surfaces of the supporting structure to tactic poly(vinyl alcohol) while substantially retaining the complex geometric configuration of the structure.

A feature of the invention is that the hydrophilic polymeric shell may be prepared using readily available materials reacted at minimally elevated temperatures and pressures.

It is another feature of the invention that the extremely thin hydrophilic polymeric shell of tactic hydrophilic poly(vinyl alcohol) envelops all outer surfaces of the supporting structure and any available interior surfaces without blocking or clogging such pores or interstices or otherwise substantially altering the complex geometric configuration of the supporting structure.

It is another feature of the invention to provide a tactic hydrophilic poly(vinyl alcohol) shell on a supporting structure which has hydroxyl reactive sites available for further reaction.

It is an advantage of the invention that articles produced according to the present invention have a surface shell which is permanent in the presence of aqueous systems or organic solvents, including those employed during use of a hydrophilic article.

It is another advantage of the invention that the tactic, hydrophilic poly(vinyl alcohol) shell provides increased mechanical strength to the polymeric structure, thereby enhancing the stability and sturdiness of an otherwise delicate film, membrane, web, or other structure while substantially retaining the physical configuration of that structure.

The invention also provides a method to form permanent and undistorted images in receptive media using image-forming substances.

An "image" is at least one pattern or character, depiction, or a combination of patterns, characters, or depictions which is formed for informational utilization or artistic pleasure.

An "image-forming substance" is an ink or other dispersion comprising pigment suspended in a liquid vehicle, a dye in solution, or a sublimable ink or dye.

The present invention provides a method for preparing a permanent and undistorted image of an image-forming substance in a medium. The method comprises loading the image-forming substance into a porous, polymeric receptive medium in at least one location to form an image. The receptive medium is made of a polymer which may receive the image-forming substance into pores of the receptive medium. Then, the receptive medium is heated to a temperature sufficient to fuse pores of the receptive medium and restructure the receptive medium into an essentially transparent film encapsulating the image in each location where the image was loaded.

The present invention also provides a method of using porous polymeric structures as receptive media for preparation of permanent and undistorted images according to the method just described.

The present invention also provides a permanent and undistorted image in a transparent, polymeric structure comprising at least one image-forming substance forming the image within at least one location in the transparent structure according to the method just described.

The present invention overcomes the deficiencies in the prior art by providing hydrophilic or hydrophobic porous structures to serve as a receptive media into which at least one image-forming substance may be loaded.

The present invention also overcomes the deficiencies in the prior art by providing a method of restructuring the receptive medium to provide a tamper-resistant and smear-resistant image.

Thus, the present invention loads a liquid based or sublimable image-forming substance into a compatible porous receptive medium and fuses the medium to render an image in the receptive medium which is permanent and undistorted.

A feature of the invention is the ease of forming a permanent and undistorted image using image-forming substances loaded into a porous receptive medium, which is fused around such image-forming substances in the location(s) desired to form the image.

Another feature of the invention is the selection of a porous receptive medium which has hydrophilic surfaces in order to load aqueous-based image-forming substances that can not be used with hydrophobic receptive media.

It is an advantage of the invention that the permanent and undistorted images formed in receptive media are tamper-resistant and smear-resistant.

The present invention also provides an oxygen scavenger to protect oxygen sensitive products. The oxygen scavenger comprises a hydrophilic porous supporting structure having a complex geometric configuration of porous surfaces and an enzyme system loaded on said surfaces to catalyze at said surfaces the reaction of a substrate, oxygen, and if necessary, water or moisture, to consume the oxygen.

The present invention also provides an oxygen scavenging package to protect an oxygen sensitive product. The package comprises a container capable of being sealed to minimize intrusion of molecular oxygen into the container and the oxygen scavenger.

"Enzyme system" means an enzyme or a mixture of an enzyme and a substrate or other compounds. The enzyme system catalyzes a reaction between oxygen, a substrate, and if necessary, water or moisture, to form a converted substrate. Most often, a sugar is the substrate which is converted by reaction with oxygen and water to form a sugar acid. The enzyme catalyzed reaction consumes oxygen and continues to scavenge oxygen from the reaction environment.

The present invention also overcomes the deficiencies in the prior art by providing a hydrophilic porous supporting structure having a complex geometric configuration into which an enzyme system may be loaded without the need for a water-dispersible binder.

Preferably, the hydrophilic porous structure may be a porous structure which is enveloped by an extremely thin self-interlocking shell of tactic, hydrophilic homopolymer or copolymer of poly(vinyl alcohol) while substantially retaining the complex geometric configuration of the porous supporting structure. Because hydrophilic surfaces are wet by the water-miscible solvent used to load the enzyme system, the hydrophilic porous supporting structure may then be loaded with an enzyme system, to react with oxygen present within a package containing an oxygen sensitive product. The tactic poly(vinyl alcohol) shell may be either syndiotactic or isotactic.

Thus, the present invention allows the hydrophilic porous supporting structure to be loaded with an enzyme system within the complex geometric configuration of the porous structure in order to catalyze an oxygen scavenging reaction.

The invention also overcomes problems confronted in the prior art by providing a method for loading of an enzyme system on hydrophilic surfaces without denaturing the enzymatically active material. The method employs applying a tactic, polymeric poly(vinyl alcohol) precursor on surfaces of the porous supporting structure, and then causing, in-situ, a hydrolysis with a hydrolysis reagent to form a tactic, hydrophilic poly(vinyl alcohol) shell enveloping such surfaces while retaining the complex geometric configuration of the porous supporting structure. The method continues with the loading of the enzyme system in a water-miscible solvent system which wets the hydrophilic shell on such surfaces and the drying of the solvent to form a layer of the enzyme system on such surfaces.

The present invention also provides a method for loading an enzyme system in a water-miscible solvent on hydrophilic complex surfaces of a porous supporting structure without denaturing the enzyme system.

A feature of the invention is the ease of loading an enzyme system on all available surfaces of a hydrophilic porous supporting structure under minimally elevated temperatures and pressures without denaturing the enzyme system.

It is an advantage of the invention that hydrophilic porous supporting structures have surfaces which readily wet to accept both an enzyme system in a water-miscible solvent and any water needed for an enzyme catalyzed reaction.

It is another advantage of the invention that hydrophilic surfaces of the porous supporting structure, having a non-denatured enzyme system loaded thereon, provide reactive sites throughout all available surfaces of the structure.

It is another advantage of the invention that the enzyme system need not be in direct contact with moisture in the oxygen sensitive product being protected, as required by prior systems, because moisture can permeate into the pores of the hydrophilic surfaces of the porous structure.

For a greater appreciation of embodiments of the invention, a detailed description follows with reference to the drawing.

BRIEF DESCRIPTION OF THE DRAWING

FIG. 1a is a scanning electron photomicrograph of the outer surfaces of a supporting structure made according to U.S. Pat. No. 4,539,256 without a tactic, hydrophilic poly(vinyl alcohol) shell thereon.

FIG. 1b is a scanning electron photomicrograph of the outer surfaces of a supporting structure with a tactic, hydrophilic poly(vinyl alcohol) shell thereon made according to the present invention.

FIG. 3b is an exploded view of another illustration of the enveloped polymeric structure of FIG. 3a.

FIG. 9b is an exploded view of the receptive medium microstructure shown in FIG. 9a.

FIG. 12a is an illustration of a hydrophilic membrane microstructure with an enzyme system loaded thereon.

FIG. 12b is an illustration of an exploded view of the hydrophilic membrane microsturcture of FIG. 12a.

EMBODIMENTS OF THE INVENTION

Supporting Structure

Figure 2A:
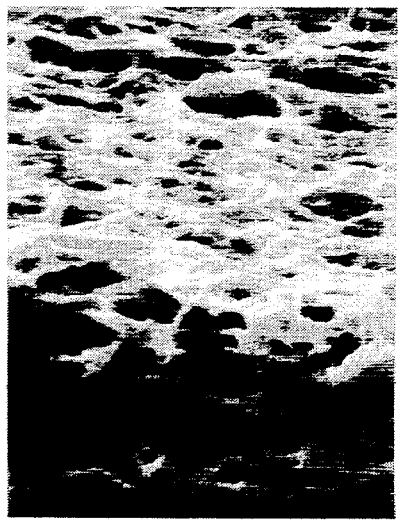
FIG. 2a is a scanning electron photomicrograph of the outer and cross-sectional surfaces of a polymeric structure made according to U.S. Pat. No. 4,539,256 without a tactic, hydrophilic poly(vinyl alcohol) shell thereon.

The supporting structure may be composed of any individual or combination of compositions of polymeric, ceramic, cellulosic, glassy, metallic, or carbonaceous materials. These materials may be either hydrophobic or hydrophilic in nature.

The supporting structure has a complex geometric configuration at a micron scale and may be formed according to known techniques into membranes, films, woven and non-woven webs, beads, spun threads, porous fibers, porous hollow fibers, or any other three dimensional configuration having a topography which permits the poly(vinyl alcohol) shell to envelop surface(s) of the structure in a self-interlocking fashion.

Non-limiting examples of the types of surfaces which can be enveloped include reticulated porous microstructures and tentacular outer surfaces of a structure.

Desirably, surfaces of any of these supporting structures provide a greater surface area per unit mass than that apparent from the gross Euclidean dimensions of the supporting structure. Many uses of articles are dependent on providing a large surface area per unit mass. The hydrophilic polymeric shell of the present invention imparts hydrophilicity without reducing substantially the surface area of the supporting structure.

Polymeric structures are preferred supporting structures. Of polymeric structures, porous membranes are preferred. More preferably, these porous membranes are microporous.

The effective pore sizes of the structure may be at least several times the mean free path of flowing molecules, e.g., from about a nanometer to about several micrometers. The porous membrane has a reticulated surface structure throughout its mass, which provides surface(s) for enveloping the complex geometric configuration of the membrane with a tactic, hydrophilic, poly(vinyl alcohol) shell.

The polymeric structure may be made from any polymeric material which may be formed into a desired complex geometric configuration.

Non-limiting examples of the polymeric materials used to make polymeric structures are: polysulfones, polyethersulfones, poly(2,6-dimethyl-4-phenylene oxide) and derivatives thereof, polyamides, polyimides, polyetherimides, polyolefins, polyhalo olefins (especially polytetrafluoroethylene), polyesters, nylon, and the like.

Non-limiting examples of suitable polyolefins include (regardless of molecular weight) polyethylene, polypropylene, poly-3-methyl-1-butene, poly-4-methyl-1-pentene, copolymers of ethylene, propylene, 3-methyl-1-butene, or 4-methyl-1-pentene with each other or with minor amounts of other olefins, e.g., copolymers of ethylene and propylene, copolymers of a major amount of 3-methyl-1-butene, and a minor amount of a straight chain n-alkene having from 2 to 18 carbon atoms such as 1-octene, 1-hexadecene, and octadecene or other relatively long chain alkenes, as well as copolymers of 3-methyl-1-pentene, and any of the same alkenes mentioned previously in connection with 3-methyl-1-butene.

A polyolefinic material may also include small amounts of other materials which may be copolymerized or blended therewith, but which do not substantially adversely affect the characteristics of the polyolefinic material.

The material comprising the polymeric structure should have a weight average molecular weight greater than about 1000, and preferably greater than about 50,000, a melt index less than about 1200 grams/10 minutes and preferably less than about 10 grams/10 minutes as measured according to ASTM D1238-82.

When the polymeric structure takes the form of a porous or microporous membrane or other porous configuration, the polymeric structure should have a porosity of from about 15 percent to about 99 percent, and preferably from about 30 percent to about 95 percent. The porosity measurements are made according to ASTM D-792.

When the polymeric structure takes the form of a membrane or other porous configuration, the structure should have an effective pore size in micrometers, measured according to ASTM F-316, of from about 0.01 $\mu$m to about 20 $\mu$m, and preferably from about 0.1 $\mu$m to about 1.2 $\mu$m.

Tactic, Hydrophilic Poly(vinyl Alcohol) Shell

The tactic, hydrophilic poly(vinyl alcohol) is prepared by the reaction of a tactic, polymeric poly(vinyl alcohol) precursor with a hydrolysis reagent. The tacticity of the poly(vinyl alcohol) ranges from about 50 percent tactic triads to about 80 percent tactic triads using Fluorine NMR spectroscopy methods. Pritchard et al., "Fluorine NMR Spectra of Poly(vinyl Trifluoroacetate)" J. Poly. Sci. 4, 707–712 (1966), incorporated by reference herein, discloses calculation of triad tacticities for poly(vinyl alcohol) prepared by various methods.

The extremely thin shell of poly(vinyl alcohol) enveloping surface(s) of a supporting structure is described in terms of monolayers of poly(vinyl alcohol) on complex surfaces of a supporting structure. A "monolayer" is the thickness of the smallest dimension of a crystalline unit cell of poly(vinyl alcohol), about 2.53 Angstroms. The poly(vinyl alcohol) shell may comprise greater than an average of 10 monolayers to impart hydrophilicity to the complex geometric and often hydrophobic surfaces of a supporting structure.

The "extremely thin" self-interlocking shell of poly(vinyl alcohol) imparting hydrophilicity does not appreciably swell upon exposure to water to substantially alter the complex geometric configuration of a supporting structure.

Reference to an "average of" a number of monolayers compensates for the fact that these extremely thin shells are not of exact uniform thickness throughout the entire complex geometric configuration of the supporting structure.

If the supporting structure is porous and it is desired not to block or clog such pores of a nominal 2 micron pore size, the poly(vinyl alcohol) shell may comprise from about an average of about 10 to about 4,000 monolayers. Desirably, the poly(vinyl alcohol) shell may comprise from about an average of 10 to about an average of 400 monolayers. It is presently preferred that the poly(vinyl alcohol) may comprise from about an average of 10 to about an average of 40 monolayers.

Based on the dimensions of pore size of a porous supporting structure and the monolayers of poly(vinyl alcohol) enveloping surfaces of that supporting structure, it is desirable to have a shell of tactic poly(vinyl alcohol) occupy less than 30 percent of the pore size existing in the supporting structure prior to forming such poly(vinyl alcohol) shell. Preferably, the tactic poly(vinyl alcohol) occupies less than 15 percent of the original pore size.

The tactic, hydrophilic poly(vinyl alcohol) shell is relatively insoluble in water or highly polar organic solvents, or nonpolar organic solvents. Such organic solvents include without limitation, dimethylsulfoxide, glycerol, ethylene glycol, and other solvents having a solubility parameter differential from poly(vinyl alcohol) of greater than about 0.4 and desirably greater than about 0.6. The solubility parameter δ (H) for poly(vinyl alcohol) is about 12.6. A tactic poly(vinyl alcohol) shell of the present invention resists some washings by solvents having solubility parameters of less than about 12.2 or greater than about 13.0. Moreover, the tactic poly(vinyl alcohol) shell resists repeated washings by solvents having solubility parameters of less than about 12.0 or greater than about 13.2. Solubility parameters for solvents may be found in the *Handbook of Chemistry and Physics*, 60th Edition, Chemical Rubber Company. The tactic, hydrophilic poly(vinyl alcohol) shell of the present invention resists washout by any of the above-named solvents.

Desirably, the initial solubility of the hydrophilic poly(vinyl alcohol) shell when exposed to the above-named solvents is less than about 1 part per 100 parts of solvent at room temperatures and pressures with no measurable solubilization thereafter. Such relative insolubility of the poly(vinyl alcohol) shell in water and polar and nonpolar organic solvents provides continuing hydrophilicity of the article during usage in the presence of such solvents.

Polymeric Poly(Vinyl Alcohol) Precursor

The poly(vinyl alcohol) precursor may be a tactic homopolymer of vinyltrifluoroacetate, a tactic copolymer of vinyltrifluoroacetate monomer and monomer(s) having a vinylic group therein, a tactic homopolymer of vinyl tert-butyl ether, or a tactic copolymer of vinyl tert-butyl ether monomer and monomer(s) having a vinylic group therein.

The weight average molecular weight of the homopolymer or copolymers of poly(vinyltrifluoroacetate) range from about 50,000 to about 2,000,000 and desirably range from about 500,000 to about 1,000,000. Desirably, the syndiotactic homopolymer or syndiotactic copolymer of poly(vinyltrifluoroacetate) is unbranched.

The weight average molecular weight of the homopolymer or copolymers of poly(vinyl tert-butyl ether) range from about 25,000 to about 60,000 and desirably from about 35,000 to about 45,000.

Non-limiting examples of monomers having a vinylic group therein, useful for copolymerization to form the precursor, include vinyl esters having up to six carbon atoms, vinyl ethers having up to eight carbon atoms, and disubstituted ethylenes (such as esters or anhydrides of lower alkyl ($C_1$–$C_4$) substituted or unsubstituted dicarboxylic acids having up to eight carbon atoms). Of these possible monomers, maleic anhydride and vinyl acetate are preferred.

The presently preferred precursor is syndiotactic poly(vinyl trifluoroacetate) homopolymer.

The precursor typically is hydrophobia and is applied in relatively dilute solution. The solvent may be any liquid that wets the surfaces of the supporting structure and solubilizes the precursor.

A solvent which allows spontaneous wetting of the precursor solution on all available surfaces of a hydrophobic supporting structure is preferred. The term "all available surfaces" includes without limitation, the reticulated pores and interstices of a porous hydrophobic article or the tentacular surface of a film, bead or web. Spontaneous wetting provides rapid, even envelopment of all of the available internal and external surfaces of the article, and an application of at least an average of 10 monolayers thickness of the precursor on such surfaces for further processing. It is possible for a porous supporting structure to have some pores having radii smaller than the hydrodynamic radius of the precursor. The surfaces along such smaller pores may not be available for application of the precursor, because the precursor molecule is too big to enter the pore.

The concentration of the precursor in solution determines the ability of the precursor to cover all available surfaces of the supporting structure while substantially retaining the complex geometric configuration of the supporting structure. The concentration of the precursor in the solvent may range from about 0.5 percent (w/v) to about 15 percent (w/v). Desirably, the concentration ranges from about 2 percent (w/v) to about 10 percent (w/v). Preferably, the concentration ranges from about 3 percent (w/v) to about 8 percent (w/v).

The solvent is desirably organic and has a significant vapor pressure at a temperature of less than about 38° C.

When the supporting structure is hydrophobic, the solvent may be any liquid which solubilizes the precursor and wets the supporting structures' surfaces. Non-limiting examples include: ketones, esters, ethers, nitriles, or amides having aliphatic, alicyclic, or aromatic groups. Of these solvents, acetone, ethyl acetate, cyclohexanone, tetrahydrofuran, pyridine, acetophenone, and acetonitrile are desired. Of these solvents, acetone is preferred due to its availability, cost, and handling.

Hydrolysis Reagent

The hydrophobic polymeric poly(vinyl alcohol) precursor applied to the surfaces of the supporting structure is converted, in-situ, to tactic poly(vinyl alcohol) by a hydrolysis reagent which is capable of converting the pendant trifluoroacetate groups of the precursor into hydroxyl groups. The hydrolysis reagent may be applied in either a liquid or a gaseous state. The hydrolysis reagent may be acidic or basic, but desirably it is basic. Thus, a desirable hydrolysis reagent has a pH of greater than about 7.0 and desirably from about 8 to about 10.

Non-limiting examples of a hydrolysis reagent include sodium hydroxide in methanol, sodium carbonate in a methanol/water solution, ammonium hydroxide in methanol, potassium hydroxide in a methanol/water mixture, and aqueous or vaporous ammonia. Of these reagents, ammonia is preferred in the vapor phase or in a methanol/water mixture.

When vaporous ammonia is used, it is presently preferred to hydrate the surfaces of the supporting structure and the shell of tactic poly(vinyl alcohol) with water or moisture vapor to stabilize hydrophilicity of the shell. Otherwise, it is possible for the extremely thin shell of poly(vinyl alcohol) to conformationally rearrange, causing loss of some or a substantial portion of hydrophilicity, if such article is not placed into use in aqueous-based solvents within weeks after manufacture of the hydrophilic article.

The amount of contact between the hydrolysis reagent and the precursor should be sufficient in duration and in concentration to permit complete conversion of the tactic precursor to tactic poly(vinyl alcohol). Desirably, the polymeric supporting structure having the precursor applied to its surfaces is immersed in a solution containing the hydrolysis reagent having a pH of greater than 7.0.

Method to Make the Article

The manufacture of an article having a hydrophilic polymeric shell varies according to its composition and its ultimate shape.

The supporting structure may be formed from commercially available materials depending on form and composition desired by those skilled in the art.

Raw materials suitable as base materials for supporting structures are commercially available. For example, polymeric supporting structures may be prepared from commercially available resins using a variety of extrusion, membrane preparation, or film-forming techniques well known in the art. A preferred method of membrane preparation is disclosed in U.S. Pat. No. 4,539,256, the disclosure of which is incorporated by reference herein.

Membranes of polysulfone are commercially available from Schleicher and Schuell of Keene, N.H. Polyolefinic microporous membranes are commercially available from Hoeschst-Celanese of Charlotte, N.C. and references to the methods of manufacture of such polyolefinic microporous membranes may be found in U.S. Pat. Nos. 4,501,793 and 3,853,601, both of which are incorporated by reference herein.

For the poly(vinyl alcohol) precursor, a poly(vinyl trifluoroacetate) homopolymer may be made according to U.S. Pat. No. 2,436,144, incorporated by reference herein. A poly(vinyl trifluoroacetate) copolymer may be made according to U.S. Pat. No. 2,436,144 or according to co-assigned U.S. Pat. Nos. 4,528,325, and 4,618,649, both of which are incorporated by reference herein.

Vinyltrifluoroacetate and comonomers for synthesis of poly(vinyltrifluoroacetate) are commercially available from Polysciences of Warrington, Pa. and Aldrich Chemical of Milwaukee, Wis.

A solution of tactic, poly(vinyl alcohol) precursor in a solvent which wets the supporting structure is then applied onto all available surfaces of the supporting structure, saturating the complex surfaces. Upon evaporation of the solvent, a self-interlocking shell is formed which substantially retains the complex geometric configuration of the structure.

Depending upon the configuration of the supporting structure and its composition, the method of application of precursor solution may involve wiping, dipping, rolling, knifing or extruding steps as the case-permits. The solvent may be removed by drying the polymeric shell for such times and at such temperatures and pressures to fully dry the precursor. Processing conditions may be controlled as necessary to permit drying of the precursor on surfaces without covering or clogging available porous surfaces of the supporting structure. The application of precursor may occur batch-wise or continuously according to the manufacturing processing conditions preferred.

For example, to prepare an unclogged porous membrane, the in-situ conversion of tactic precursor to tactic, hydrophilic poly(vinyl alcohol) occurs by hydrolysis at less than about 38° C. using a hydrolysis reagent in either liquid or vaporous phase. A closed reaction vessel for vaporous reaction is preferred. A dipping tank for liquid reaction is preferred.

When ammonia vapor is used, after a closed vessel is employed, the membrane is dipped or sprayed with water or moisture vapor to lock in hydrophilicity of the poly(vinyl alcohol) shell.

While it is preferable to provide hydrophilic surfaces for the supporting structure, it can be desirable in certain articles to be able to reverse hydrophilicity into hydrophobicity after a process step or other intermediate activity. Hydrophilic shells of poly(vinyl alcohol) of the present invention can be conformationally rearranged into hydrophobic surfaces by heating the hydrophilic supporting structure above the glass transition temperature (Tg) of poly(vinyl alcohol), about 80 degrees C., for a limited period of time. Without being limited to a particular theory, it is believed that the increased mobility of poly(vinyl alcohol), above its Tg, allows a conformational rearrangement of hydroxyl groups at outer surfaces of the shell to point in towards the bulk of the shell. The driving force for this rearrangement is a natural desire to minimize interfacial energy (i.e., between the shell surface and air). This results in the outermost few Angstroms of the shell surface being defined by the hydrocarbon backbone of the poly(vinyl alcohol). Since "wetting" and hydrophilicity is defined by the outermost few Angstroms of a surface, the presence of the hydrocarbon backbone in place of hydroxyl groups results in the surface no longer being hydrophilic. Thus, the shell has the same chemistry but is hydrophobic.

Hydrophobic poly(vinyl alcohol) can be converted to hydrophilic poly(vinyl alcohol) by wetting surfaces of the shell-covered supporting structure with a polar, water-miscible solvent, such as methanol or acetone, followed by solvent exchanging water into pores of the supporting structure and drying. In such re-hydrophilization, contact of a poly(vinyl alcohol) shell with such polar, water miscible solvent re-orients hydroxyl groups out from such surfaces. Water or moisture vapor plasticizes poly(vinyl alcohol), swells such shell, and lowers the glass transition temperature thereof in the presence of such a polar environment.

Thus, according to methods of the present invention, one can control hydrophilization of supporting structures, throughout all surfaces, only at outer surfaces, or only in pores or interstices. One can create regiospecific hydrophilic surfaces for a supporting structure according to need. Non-limiting examples of such regiospecific surfaces can be patterned hydrophilicity throughout specific portions of a porous membrane, "facade" hydrophilicity of a porous membrane, or a "sandwich" hydrophilicity having hydrophobic inner pores and interstices.

Alternatively, regio-specific hydrophilization can be achieved by introducing a hydrolysis reagent only to designated portions of surfaces of a supporting structure covered with polymeric poly(vinyl alcohol) precursor. Also, such regio-specific hydrophilization can be achieved by applying polymeric poly(vinyl alcohol) precursor to designated portions of surfaces of the supporting structure, followed by hydrolysis of such portions with hydrolysis reagent.

However, some uses of the article may prefer skinned, covered or clogged pores, to convert a fractal geometric configuration of the article to a Euclidean geometric configuration. In such circumstances, processing conditions or solutions may be adjusted as desired. Three parameters may be adjusted. Choice of solvent influences rate of coverage and evaporation. Precursor concentration determines solution viscosity, rate of pore penetration, and shell thickness. Pore sizes of surfaces of the article also determine rate of pore penetration.

FIG. 1 illustrates the comparison between a hydrophobic microporous membrane (prepared according to Example 23 of U.S. Pat. No. 4,539,256) and a microporous membrane having with tactic, hydrophilic poly(vinyl alcohol) shell (prepared according to the present invention). The outer surfaces of the article in scanning electron photomicrograph 1a are hydrophobic and untreated. The outer surfaces shown in scanning electron photomicrograph 1b are hydrophilic due to the tactic, hydrophilic poly(vinyl alcohol) shell about its surfaces. The treated membrane shown in scanning electron photomicrograph 1b retains its fractal geometric configuration because its complex surfaces are substantially as open and unclogged as the unprocessed membrane in photomicrograph 1a. Thus, the pores and interstices of supporting structure are not filled or occluded by the in-situ generated poly(vinyl alcohol) shell. The fractal configuration of the supporting structure is not converted to a Euclidean configuration. Thus, the membrane retains its structural advantages while adding hydrophilic surfaces.

Figure 2B:
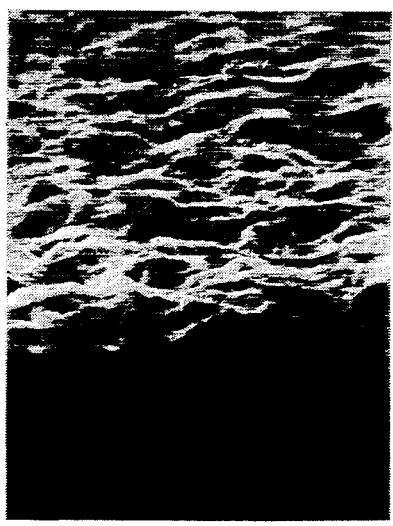
FIG. 2b is a scanning electron photomicrograph of the outer and cross-sectional surfaces of a polymeric structure with a tactic, hydrophilic poly(vinyl alcohol) shell thereon made according to the present invention.

FIG. 2 illustrates that a microporous membrane having a tactic, hydrophilic poly(vinyl alcohol) shell enveloping both outer and inner porous surfaces of the membrane does not clog or occlude any pores or interstices. Scanning electron photomicrograph 2a of the same hydrophobic membrane as in FIG. 1a and scanning electron photomicrograph 2b of the same hydrophilic membrane as in FIG. 1b both show about 10 microns of cross-section of the membrane at the top of the scanning electron photomicrographs, with the remainder being a perspective view of the outer surface. No significant difference can be seen between these two photos.

Figure 3A:
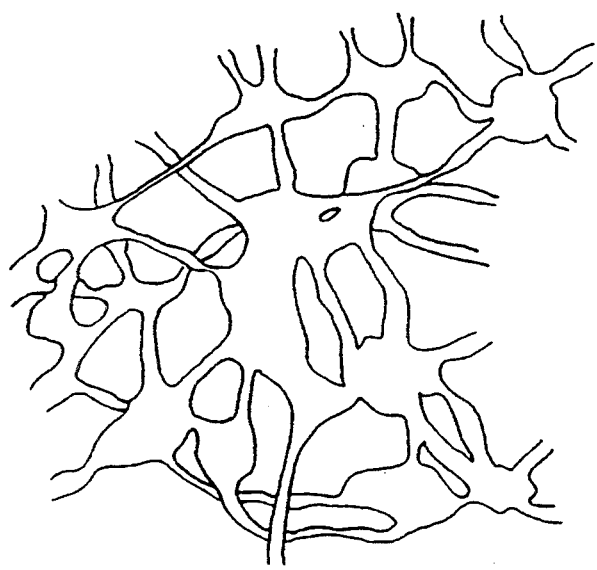
FIG. 3a is an illustration of a membrane microstructure which is enveloped by a poly(vinyl alcohol) shell.
Figure 3B:
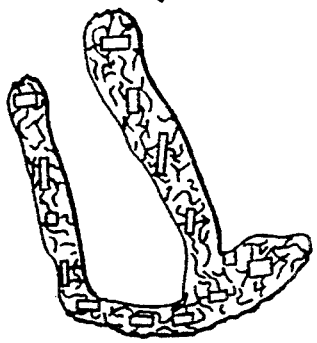

While not being limited to any particular theory, it is believed that the shell of tactic poly(vinyl alcohol) envelops available surfaces of the supporting structure by forming tie molecules among crystallite molecules. FIG. 3a illustrates a membrane microstructure which is enveloped by a poly(vinyl alcohol) shell. The exploded view of FIG. 3b provides another illustration of the enveloped polymeric structure. Tie molecules of poly(vinyl alcohol), such as those described in Basset, D.C., *Principles of Polymer Morphology*, Cambridge Univ. Press, 1981, between crystallites of poly(vinyl alcohol), provide the self-interlocking strength of the shell. The complex geometric configuration of the underlying polymeric structure is substantially retained after envelopment of from about an average of 10 to about an average of 4000 monolayers of poly(vinyl alcohol) and desirably from about an average of 10 to about an average of 400 monolayers of poly(vinyl alcohol).

Usefulness of the Invention

The hydrophilic supporting structures of the present invention can be utilized in several applications involving aqueous fluids or hydrophilic organic solvents. The chemical inertness and complex geometric configuration of many hydrophobic materials or structurally weak hydrophilic materials would make them ideally suited for hydrophilic processes if the supporting structure had hydrophilic surfaces of a self-interlocking shell.

Having a tactic, hydrophilic poly(vinyl alcohol) shell enveloping surfaces of such hydrophobic supporting structures enables such structures to be used in aqueous systems or in hydrophilic organic solvents in which the untreated supporting structure above would be inadequate, incompatible, or ineffective, notwithstanding its complex geometric configuration desired for such mechanical processes. The relative insolubility of the tactic, hydrophilic poly(vinyl alcohol) shell in a large number of organic solvents and water enables the article to be used in those circumstances where the solvent must wet the article in order for the article to perform its intended purpose. A useful measure of "wetting" capability is pore wetting surface energy.

"Pore wetting surface energy" means the surface energy of the supporting structure required for spontaneous wetting of a pore through the wicking of water into the pore via capillary forces. Spontaneous wetting of the pore occurs when the surface energy of the internal surface of the pores is high enough for water to have less than a 90° contact angle with the surface. Analytically, according to Wu, S., *Polymer Interface and Adhesion*, Marcel Dekker, New York, 1982, p. 244, spontaneous wetting occurs when the capillary force, $\Delta P_c$, in the following equation is positive:

$$\Delta P_c = 2\sigma_L \cos \Theta / r$$

where $\sigma_L$ is liquid surface tension (72.8 dynes/cm for water), $\Theta$ is the contact angle ($<90°$), and r is the pore radius.

The magnitude of the positive capillary force correlates to the rate of spontaneous wetting. The variation in pore size and complex geometric configuration also assists in controlling the rate of migration.

The tactic, hydrophilic poly(vinyl alcohol) shell enveloping the supporting structure also provides the advantage of increasing the mechanical strength of a supporting structure. By enveloping internal and external surfaces of a membrane while substantially retaining the complex geometric configuration of the membrane (e.g., a microporous membrane having pore sizes of from about 0.01 $\mu$m to about 1.2 $\mu$m,) the tactic poly(vinyl alcohol) shell increases the tensile strength and percent elongation properties of the supporting structure. While not limited by any particular theory, it is believed that the enhanced tensile strength is achieved by the covering of acute geometric interstices of the fibrillar structure which would otherwise be probable stress concentration points for failure initiation in the complex geometric configuration. While acute geometric interstices may be lessened, the overall complex geometric configuration is substantially retained.

The presence of a tactic, hydrophilic poly(vinyl alcohol) shell about a supporting structure provides highly reactive hydroxyl sites for further chemical, physical, and biological uses.

The present invention has broad utility in that articles having durable hydrophilic polymeric shells can be prepared from a wide variety of supporting structure materials which can comprise any of several compositions and take any of several forms. The present invention's ability to provide articles having a non-crosslinked self-interlocking shell comprising hydroxyl functionality that displays minimal solubility in water and aqueously soluble organic solvents provides advantages not previously found in the art.

Membrane Filters

Hydrophilic microporous polyolefinic membranes have utility as membrane filters to separate solids from fluids. A normally hydrophobic polyolefinic microporous membrane has a complex geometric configuration because of a multiplicity of fractal surfaces defining pores and interstices. Application of a tactic, hydrophilic poly(vinyl alcohol) shell to the polyolefinic membrane converts its normally hydrophobic surfaces to hydrophilic surfaces without substantially altering the complex geometric configuration of the membrane.

When placed in a filtration chamber, the membrane is placed across the path of fluid flow to provide a separation barrier to separate particulate material from the fluid. The membrane provides a physical barrier based on the complex geometric configuration of the supporting structure while relying on the hydrophilicity of the poly(vinyl alcohol) shell to allow the fluid to readily wet the membrane surface and maintain acceptable flow rates through the membrane.

Membrane filters of the present invention may be symmetric or asymmetric in pore size distribution through the membrane cross-section. Asymmetric membranes are preferred because they typically have a higher permeability than a symmetrical membrane of similar particle retention.

Membrane filters of the present invention may be reticulated or granular. Reticulated membranes are preferred because such membranes generally have a higher porosity than granular membranes. The network of open interstitial flow channels around fibrous strands of a reticulated membrane provide greater permeability of water than the porous network formed around coalesced solid particles of a granular membrane.

Effective pore sizes of a membrane filter of the present invention may range from about 0.01 $\mu$m to about 20 $\mu$m. Depending on the pore size of the supporting structure, the membrane filters of the present invention can be used in either ultrafiltration or microfiltration applications.

The present invention provides a low cost membrane having desirable porosity and pore sizes which has a shell of hydrophilicity enveloping its surfaces. The poly(vinyl alcohol)-shelled porous membrane filters of the present invention have physical strength properties at least comparable to those of the polyolefin support structure which enables it to endure considerable volumes of fluid passing through the membrane under high pressure without tearing, rupturing, or the like.

Nonlimiting examples of filtration uses for membranes of the present invention include filtration of biological fluids, (e.g. bacteria filtration), cold pasteurization, water polishing for pharmaceuticals and electronics.

Drug Delivery Devices

Microporous polyolefinic membranes could have considerable usage for controlled delivery of hydrophilic therapeutic agents if the microporous membrane were hydrophilic. The tactic, hydrophilic poly(vinyl alcohol) shell on all available surfaces of a microporous polyolefinic membrane renders the surfaces hydrophilic without substantially altering the complex geometric configuration of the membrane.

Figure 4:
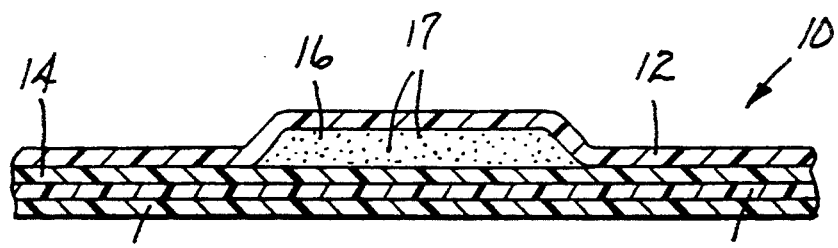
FIG. 4 illustrates a cross sectional view of a drug delivery device of the reservoir type.
Figure 5:
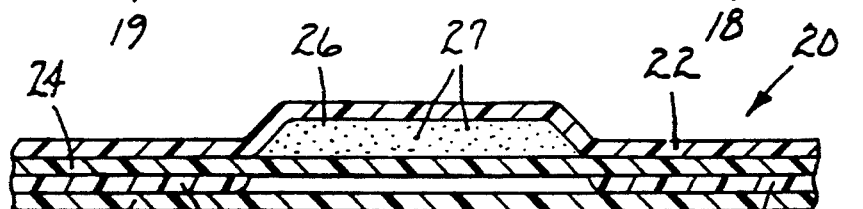
FIG. 5 illustrates a cross sectional view of another embodiment of a drug delivery device of the reservoir type.
Figure 6:
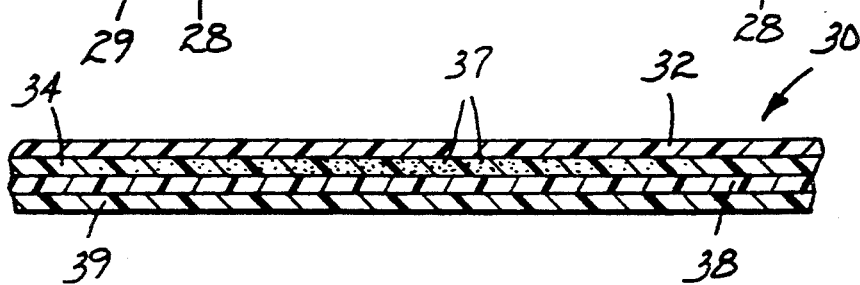
FIG. 6 is a cross sectional view of a drug delivery device of the depot type.

A drug delivery device using a hydrophilic microporous membrane as a component thereof may take several forms, such as that shown in FIGS. 4–6.

In FIG. 4, the drug delivery device 10 is shown. The device 10, useful for either topical or transdermal drug delivery, comprises a backing layer 12 sealed to a membrane 14 which forms a reservoir 16 for the therapeutic agent 17. A hypoallergenic pressure-sensitive adhesive layer 18 is coated on the membrane 14 and protected by a release liner 19.

The therapeutic agent 17 is typically hydrophilic or can benefit from the hydrophilic surface. A hydrophilic shell of tactic poly(vinyl alcohol) on a microporous membrane 14 having pore sizes of from about 0.5 $\mu$m to about 0.8 $\mu$m facilitates the migration of the therapeutic agent 17 through the membrane 14 and into adhesive 18 for delivery to the skin of a patient after release liner 19 is removed. By variation of the pore size of membrane 14, the rate of migration of therapeutic agent 17 to the skin may be controlled, so long as the rate of migration through the pressure sensitive adhesive 18 is at least as fast as the rate of migration through membrane 14.

FIG. 5 illustrates another embodiment of a drug delivery device 20. The device 20 has a backing 22 and a membrane 24 sealed to provide a reservoir 26 within which therapeutic agent 27 is stored. Hypoallergenic pressure-sensitive adhesive layer 28 extends about the perimeter of the device 20. A release liner 29 protects the pressure-sensitive layer and the membrane 24 until use is desired. An example of this construction is disclosed in U.S. Pat. No. 4,855,294.

The difference between the embodiment shown in FIG. 5 and the embodiment shown in FIG. 4 is the absence of the pressure-sensitive adhesive layer in the pathway of the therapeutic agent 27 from reservoir 26 to the skin of the patient. Thus, therapeutic agent 27 need only migrate through porous membrane 24 in order to contact the skin of the patient. The rate of migration may be controlled by selection of the microporous membrane 24 having different thicknesses and pore sizes without being limited by the rate of migration of the therapeutic agent 27 through pressure-sensitive adhesive 28.

FIG. 6 illustrates yet another embodiment of the use of a hydrophilic microporous membrane of the present invention in drug delivery device 30. In this instance, backing material 32 is sealed to membrane 34 without providing a reservoir. Rather, therapeutic agent 37 is stored within membrane 34 as a depot for subsequent delivery through pressure-sensitive layer 38 to the skin of the patient after release liner 39 is removed. The microporous complex geometric configuration of the membrane 34, the thickness of the membrane 34 and the cell dimensions of the pores may be adjusted to accommodate certain concentrations or volumes of therapeutic agent 37 as desired for topical or transdermal delivery to or to and through the skin of the patient, respectively.

Rarely is therapeutic agent 17, 27 or 37 used alone in the drug delivery device. Excipients are often also present as solvents or penetration enhancing agents. Solvents assist the placement of the therapeutic agent in the device. Penetration enhancing agents assist the penetration of the therapeutic agent to and through the skin. These excipients also migrate through the membrane 14, 24 or 34 with the therapeutic agent 17, 27, or 37. The hydrophilicity of the membrane 14, 24 or 34 imparted by the tactic poly(vinyl alcohol) shell may also aid in excipient migration.

The membrane 14, 24 or 34 is desirably made from polyolefinic polymeric structures which can be heat sealed to the backing 12, 22 or 32, respectively, using heat sealing techniques known to those skilled in the art,. e.g. pressing between heated platens. The poly(vinyl alcohol) shell on the surfaces of membrane 14, 24, or 34 does not prevent the heat sealing of the membrane to the backing.

The backing 12, 22 or 32 can be any backing material known to those skilled in the art and useful for drug delivery devices. Non-limiting examples of such backing materials are polyethylene, ethylene-vinyl acetate copolymer, polyethylene-aluminum-polyethylene composites, and "ScotchPak TM" brand backings commercially available from Minnesota Mining and Manufacturing Company of St. Paul, Minn. (3M).

The hypoallergenic pressure-sensitive adhesive layer can be any hypoallergenic pressure-sensitive adhesive composition which may be coated on the membrane of the present invention. Non-limiting examples of pressure-sensitive adhesive compositions useful in drug delivery devices are acrylate-based pressure-sensitive adhesives disclosed in U.S. Pat. No. 4,737,559, the disclosure of which is incorporated herein by reference.

The release liner 19, 29 and 39 may be any release liner material known to those skilled in the art. Non-limiting examples of such release liners commercially available include siliconized polyethylene terephthalate films commercially available from H. P. Smith Co. and fluoropolymer coated polyester films commercially available from 3M under the brand "ScotchPak TM" release liners.

The therapeutic agent may be any water soluble or otherwise hydrophilic therapeutically active material known to those skilled in the art and approved for delivery to or through the skin of a patient. Non-limiting examples of therapeutic agents useful in transdermal delivery devices are peptides or short chain proteins, the salt form of any active drug used in transdermal applications and permeable to mammalian skin through the use of penetration enhancing agents, or growth factors for use in enhancing wound healing. Other therapeutic agents are identified as drugs or pharmacologically active agents and are disclosed in U.S. Pat. Nos. 4,849,224 and 4,855,294, and PCT Patent Publication WO 89/07951.

Excipients or penetration enhancing agents are also known to those skilled in the art. Non-limiting examples of penetration enhancing agents include ethanol, methyl laureate, oleic acid, isopropyl myristate, and glycerol monolaurate. Other penetration enhancing agents known to those skilled in the art are disclosed in U.S. Pat. Nos. 4,849,224; and 4,855,294 and PCT Patent Publication WO 89/07951.

The method of manufacturing a transdermal delivery device depends on its construction.

The drug delivery device 10 shown in FIG. 4 may be constructed using the following general method. A solution or a slurry is prepared by homogeneously mixing a therapeutic agent 17, other constituents of the reservoir (e.g., gelling agents, skin penetration enhancing agents, diluents, and other excipients), and a suitable solvent. The solution or slurry is placed into a dispenser on form fill and seal equipment. A laminate of microporous membrane 14, adhesive layer 18, and release liner 19 is constructed and passed underneath the dispenser. A pre-measured quantity of the solution or slurry is deposited from the dispenser on the laminate. Backing layer 12 is then applied over the quantity of solution or slurry. The backing layer 12 is heat-sealed to the membrane 14 around the quantity of solution or slurry, creating a reservoir 16. The resulting laminate of backing 12, reservoir 16, membrane 14, adhesive 18, and liner 19 is usually made in large sheets from which individual devices 10 of the desired shape and size may be cut.

The drug delivery device 20 shown in FIG. 5 may be made in the same manner as described in FIG. 4, except that the location(s) of the adhesive layer 28 is different. The adhesive layer 28 is pattern-coated on release liner 29 and laminated to membrane 24. The pattern-coating is arranged so that when the laminate of membrane 24, layer 28 and liner 29 is finally assembled, there is no adhesive layer 28 between the location(s) of reservoir 26 and the liner 29.

The drug delivery device 30 shown in FIG. 6 may be prepared using the following general method. A solution is prepared by dissolving the therapeutic agent 37 and such optional excipients as are desired in a suitable solvent. The membrane 34 of the present invention is immersed in or coated with the solution containing the therapeutic agent 37 to effect diffusion of the therapeutic agent and any excipient into the porous structure of the membrane 34. The resulting loaded membrane 34 is laminated to the backing layer 32. A solution, or optionally an emulsion, of the adhesive is coated onto the release liner 39 and allowed to dry to form adhesive layer 38. The exposed face of the membrane 34 is laminated to the exposed face of the adhesive layer 38 to complete the assembly. Again, the resulting laminate is usually made in large sheets from which individual devices 30 of the desired shape and size may be cut.

The usefulness of the hydrophilic microporous membranes of the present invention are not limited to drug delivery devices which are placed on the skin of a patient. Non-limiting examples of other uses include (a) construction of a device with two hydrophilic microporous membranes heat sealed together to form a reservoir pocket for drug delivery in multiple directions, such as for subdural or intra-muscular drug delivery; and (b) construction of a hydrated membrane to be used in conjunction with iontophoresis to provide a salt bridge to electrically diffuse charged active agents across the hydrophilic porous membrane and to the skin.

Electroplating Devices

Polyolefinic membranes, especially microporous polyolefinic membranes, could have considerable usage in conjunction with electroplating devices if the membrane were hydrophilic. A microporous polyolefinic membrane has a complex geometric configuration because of a multiplicity of surfaces defining pores and interstices. The tactic, hydrophilic poly(vinyl alcohol) shell on all available surfaces of a microporous polyolefinic membrane converts the hydrophobicity of the polyolefinic membrane to hydrophilicity .without substantially altering the complex geometric configuration of the membrane.

A residue barrier in an electroplating device may take the form of an anode bag to trap debris. Debris may be additives used in forming the anode and, in extremely acidic baths, bubbles of gaseous oxygen. When used as an anode bag, the membrane should be microporous.

A residue barrier may also be a diaphragm separating an anode from a cathode in the device to trap particulates and debris from a cathodized substrate being electroplated in the agitated and heated electrolytic solution. When used as a diaphragm, if there is positive pressure of electrolyte solution flow, the diaphragm may be porous. Otherwise, the diaphragm should be microporous.

A residue barrier can also be used in an electrochemical apparatus for the recovery of magnetic metals, such as nickel and iron, from synthetic diamond bearing materials dispersed in an electrolyte. In this use, it is particularly important to protect a cathode with a hydrophilic microporous membrane bag to prevent diamonds and unwanted debris being deposited with metal being recovered.

A residue barrier can also be used in an electrodeposition apparatus for plating batches of particles that either float in the electrolyte or sink, such as an electrode enclosure for use in barrel plating of small metal parts or surface conductive non-metallic parts.

Whether an anode bag, cathode bag, or a diaphragm, the residue barrier provides a physical barrier based on the complex geometric configuration of a membrane while relying on the hydrophilicity of the poly(vinyl alcohol) of the shell to maintain the electrochemical process of metallic ion transport to the substrate.

Figure 7:
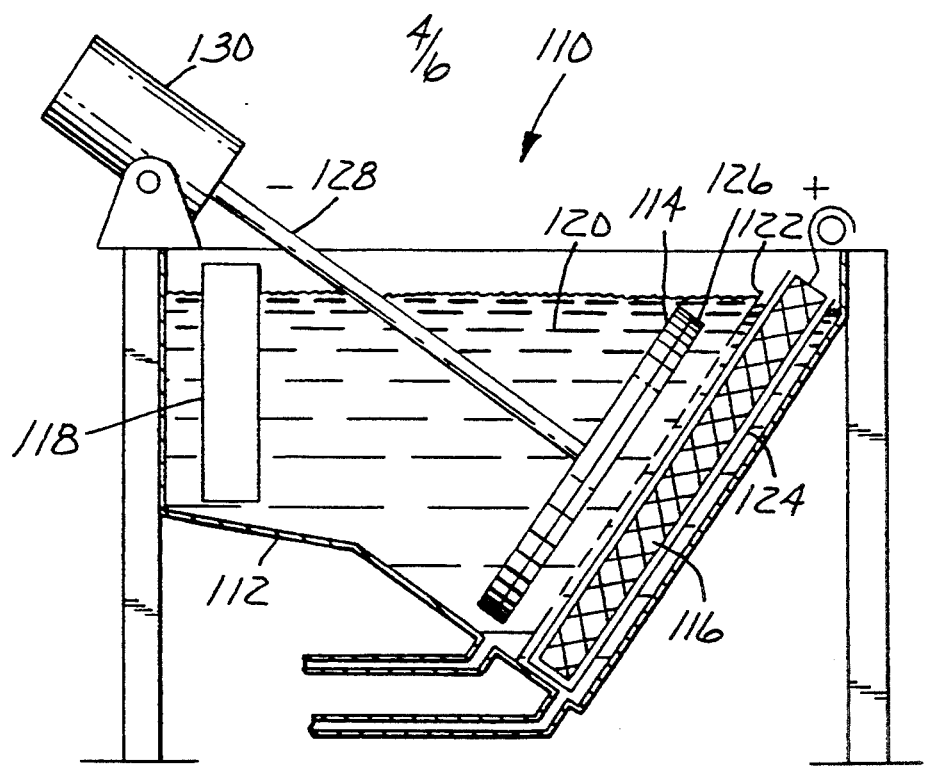
FIG. 7 illustrates a typical electroplating device having an anode bag and a diaphragm of the present invention.

In FIG. 7, a typical electroplating device 10 is shown. The device 110 is a tank 112 in which a cathode 114, an anode 116, a heater 118, and electrolyte 120 reside. Between cathode 114 and anode 116 is a diaphragm 122 of the present invention. Surrounding anode 116 is an anode bag 124 of the present invention. Preferably, the anode bag 124 also has an overlay of coarse non-woven material (not shown) to further protect the structural integrity of the bag 124 in a turbulent tank 112. Preferably, the overlay is a non-woven polypropylene.

The cathode has the substrate 126 to be electroplated positioned adjacent the diaphragm 122 and the anode 116. The cathode is often rotated on shaft 128 by turning head motor 130 to vigorously agitate the electrolyte 120 in the tank 112 and improve uniformity of deposit thickness.

The anode 116 is typically a titanium basket holding chips of the metal to be electroplated. Often, the metal is nickel or copper. The chips are typically formulated with additives useful to improve anode chip erosion and to facilitate entry of the metal into solution.

An anode bag was previously often made of cotton cloth or polypropylene fabric surrounding a napped or flannel-like interior. Anode bags are provided to contain any additives and debris from entering the electrolytic solution. Because the additives are often insoluble, these residue particulates could mar the surfaces of the electroplated substrate 126 if not contained.

An anode bag previously had pore sizes of about 10 $\mu$m or greater to attempt to contain anode additive residues. But the fabric did not block particulate residues smaller than 10 $\mu$m in size and did not restrict electrolyte solution agitation near the anode. Moreover, the prior anode bags did unfortunately create about a 8–10% reduction in electroplating current flow. Efforts to use a tighter weave anode bag further inhibited electroplating current flow because the fabric became an electrical insulator.

An anode bag 124 of the present invention may have pore size ten times smaller than the conventional fabric without substantially impairing electroplating current flow. Thus, the complex geometric configuration of the membrane blocks particulates and restricts electrolyte solution agitation near the anode without disrupting the electroplating current flow of metallic ions to the cathode substrate 126 to be electroplated.

An anode bag 124 of the present invention is especially useful for acid copper electroplating which requires grain refiner additives to harden, level, and brighten the deposit. These additives added to the electrolyte 120 deteriorate or are consumed by contact with copper anodes and copper particulates in the electrolyte 120, even without agitation. Because the anode bag 124 of the present invention restricts the flow of electrolyte solution near a copper anode, additives to the electrolyte 120 to improve the substrate 126 are inhibited from deterioration by reaction with copper at the anode. The valuable additives may be better controlled in the tank 112.

The anode bag 124 also contains gaseous oxygen formed at or near the anode when the electrolyte is a nickel-phosphorus solution. The bubbles of oxygen are impeded from blending into the electrolyte 120 in the remainder of tank 112 and rise to the surface of the electrolyte 120 within anode bag 124.

The anode bag 124 of the present invention reduces the need for constant filtering of the electrolyte 120 to remove particulate residues because the anode bag 124 contains such residues more efficiently than currently performed.

However, filtering within a tank 112 remains desirable. Diaphragm 122 of the present invention serves to skim undesired particulate residues from the electrolyte 120 without substantially disrupting electroplating current flow. Diaphragm 122 is stretched over a supporting frame in tank 112 adjacent cathode 114. Floating debris is skimmed from the cathode compartment as the electrolyte 120 overflows the diaphragm 122 into the anode compartment.

In electrolyte containing nickel, cotton cloth has been conventionally used as a diaphragm. But the deficiencies of cotton are the same as for its use as an anode bag. Further, cotton is not durable in an acid copper or an acid nickel-phosphorus electrolyte system where the pH of the electrolyte 120 may be lower than 1.

A diaphragm 122 of the present invention shows no measurable reduction in electroplating current flow. In an acid copper plating electrolyte 120, a poly(vinyl alcohol) shell polyolefin membrane diaphragm 122 is more durable than cotton cloth.

While not being limited to any particular theory, it is believed that the electroplating current flow rate is not disrupted because the pore wetting surface energy of the membrane as diaphragm 122 or anode bag 124 is greater than the surface tension of the electrolyte 120.

Thus, flow of metallic ions is unimpeded while particulate residues and other debris are physically restrained at pores of the membrane. The hydrophilicity of the shell of the membrane retains current flow while the complex geometric configuration of the membrane blocks residue.

Electrochemical Cell Separators

Polyolefin-based hydrophilic microporous membrane materials of the present invention are particularly desirable as separator materials for aqueous based electrochemical cells because they exhibit most of the performance properties that are desired for good electrochemical cell separation. More specifically, polyolefin-based hydrophilic membranes of the present invention are substantially non-conductive, chemically inert to the environment of the electrochemical cell, provide good barrier properties for electrochemical cell uses, and are hydrophilic so that they are spontaneously and rapidly wet by hydrophilic electrolyte compositions.

The polyolefin-based hydrophilic microporous membrane materials of the present invention also demonstrate excellent dimensional stability, showing less than about 5% change, and preferably less than about 3% change over a temperature range of from about ambient to about 120° C. The polyolefin-based hydrophilic microporous membrane materials of the present invention exhibit minimal resistance to electrolyte flow through the membrane due to their high porosity level. This low resistivity is due, at least in part, to the fact that very high electrolyte levels are present in the separator at all times when in the electrochemical cell. The high porosity coupled with the hydrophilic properties of the poly(vinyl alcohol) shell on available surfaces contribute to the high electrolyte levels present in the separator. The hydrophilic microporous membrane materials for an electrochemical cell separator should have a porosity of at least 15%, desirably have a porosity of at least 30%, preferably have a porosity of at least 40%, and most preferably have a porosity of at least 50%. Porosity is measured by the test method described in ASTM D792-66, the disclosure of which is incorporated by reference.

The polyolefin-based hydrophilic microporous membrane materials of the present invention offer a very attractive balance between porosity level and barrier properties desirable for electrochemical cell separators. Hydrophilic membranes having maximum pore sizes from about 0.05 to about 1.2 $\mu$m, and more preferably from about 0.09 to about 0.2 $\mu$m in diameter provide excellent barrier properties. Separators having such pore sizes minimize passage of particulate matter and other debris through the separator. It is important that the separator material exhibit good barrier and dendristatic properties so that particles or dendrites cannot bridge between opposing electrodes which can cause an electrical short and eventual failure of the electrochemical cell. Polyolefin-based hydrophilic microporous membrane materials of the present invention may possess a machine direction tensile strength of at least about 100 kg/cm$^2$, more preferably a tensile strength of at least about 200 kg/cm$^2$, and most preferably a tensile strength of at least about 350 kg/cm$^2$.

Figure 8:
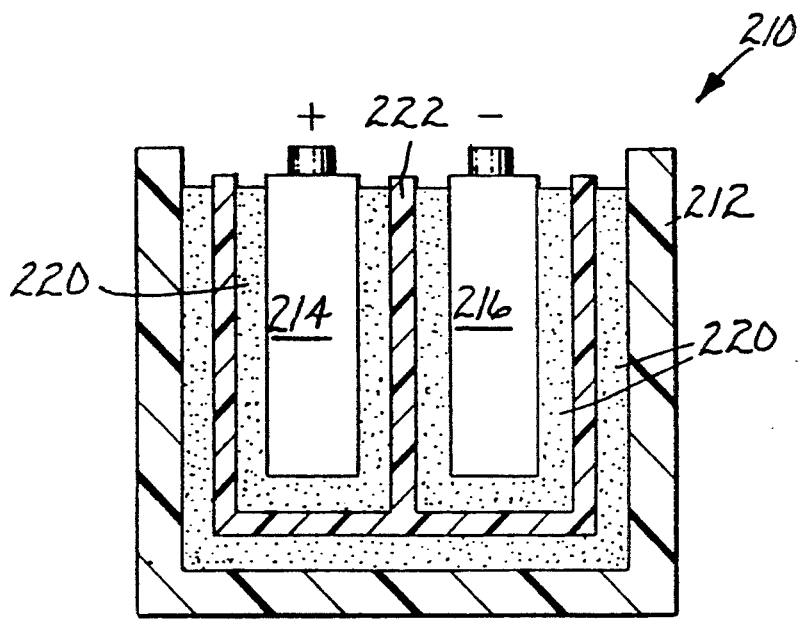
FIG. 8 illustrates a typical electrochemical cell having at least one cathode, at least one anode, electrolyte and at least one separator of the present invention.

In FIG. 8, a typical electrochemical cell 210, such as a battery is shown. The device 210 is a container 212 in which at least one cathode 214, at least one anode 216, and electrolyte 220 reside. Between each cathode 214 and each anode 216 is a separator 222 of the present invention.

An electrochemical cell separator 222 of the present invention restricts the flow of particulate matter, dendrites, or other debris between cathodes 214 and anodes 216 and preserves the electrochemical efficiency of the energy storage and energy dispensing processes during the life of the cell 210. Such debris is less likely to interfere with the electrochemical activity at cathodes 214 and anodes 216.

While not being limited to any particular theory, it is believed that the electrochemical current flow rate is not significantly disrupted because the surface energy of the membrane as electrochemical cell separator 222 is greater than the surface tension of the electrolyte 220. Flow of ions is unimpeded while particulate matter and other debris are physically restrained at pores of the membrane.

Receptive Media

The type of porous receptive medium to be used depends on the type of liquid used with the image-forming substance(s). The type of medium and the type of liquid must be compatible for the liquid to wet the porous surfaces of the medium.

If the image-forming substances are organic-based or sublimable, then hydrophobic porous materials known in the art may be used. Nonlimiting examples of hydrophobic porous materials include microporous materials disclosed in and made according to U.S. Pat. No. 4,539,256 (Shipman) and U.S. Pat. No. 4,867,881 (Kinzer), the disclosures of which are incorporated by reference. Other microporous materials identified in the Background of the Invention above may also be useful. Desirably, a hydrophobic material is a microporous polyolefin membrane. FIGS. 1a and 2a are photomicrographs of polyethylene membranes made according to Example 23 of U.S. Pat. No. 4,539,256.

If the image-forming substance(s) are aqueous-based, organic-based, or sublimable, then the receptive medium may be a hydrophilic porous material known in the prior art. Desirably, of known hydrophilic porous materials, the hydrophilic porous material disclosed in U.S. Pat. No. 4,501,793 may be used as a receptive medium, provided that the image in the medium is made permanent by fusing within 30 minutes after loading of the image-forming substance into the medium. Fusing within 30 minutes minimizes excessive bleeding of the image. Another desirable hydrophilic porous material is a microporous nylon 6,6 membrane.

Preferably, the receptive medium may be a hydrophobic porous structure having an extremely thin self-interlocking shell of tactic, hydrophilic homopolymer or copolymer of poly(vinyl alcohol) which substantially retains a complex geometric configuration of the porous supporting structure. The tactic poly(vinyl alcohol) shell may be either syndiotactic or isotactic.

A receptive medium may take any shape into which an image-forming substance may be loaded to form an image. Nonlimiting examples include spheres, cylinders, cubes, cones, boxes, sheets, tubes and the like. Desirably, a receptive medium may be curvilinear. Preferably, a receptive medium is planar.

A receptive medium may comprise the entire structure used to form a permanent image of the image-forming substance loaded into the receptive media in desired pattern(s) or character(s). Desirably, a receptive medium is laminated temporarily or permanently to a non-porous substrate.

A substrate may be transparent, translucent, or opaque, depending upon the desired relative transparency of the final laminate. Preferably, the receptive media is permanently laminated to a non-porous planar, transparent substrate such as a polymeric film.

Receptive media are generally not transparent due to light scattering among the pores of the media but can become transparent if the media are restructured to close such pores. The closing of such pores seals the image created by the loading of image-forming substance into the receptive media in the location(s) of such loading. Thus, the image is permanently formed and protected beneath the surface of the restructured receptive media.

The restructuring of the receptive media to close pores and form a film protecting the image loaded in the media may be accomplished by fusing the porous receptive media or otherwise transforming the porous media into a film. Preferably, the fusing process collapses the porous, non-transparent structure of the receptive media into an essentially transparent, fused receptive media film. The fused media film encapsulates the image loaded into the porous media prior to fusing. The temperature of fusing should not exceed a temperature which would degrade or otherwise affect the integrity of the image-forming substance. For the desired polyolefin-based receptive media, the temperature of fusing ranges from about 120° C. to about 140° C.

Once the appropriate type of receptive medium is selected for the desired image-forming substance, the volume of image-forming substance absorbable per unit area of receptive media is determined by selection of a receptive medium having a sufficient void volume, the amount of image-forming substance available for loading, and extent of the loading of the image-forming substance into the receptive medium to fill the void volume in the location(s) where the image is desired. Preferably, the image-forming substance volume absorbable, or image capacity, exceeds the image capacity used in commercially available ink-jet printers.

For suitable image capacities, the porous receptive media should have an effective pore size in micrometers, measured according to ASTM F-316, of from about 0.01 $\mu$m to about 20 $\mu$m, and preferably from about 0.1 $\mu$m to about 1.2 $\mu$m.

The receptive media should have a porosity of from about 15 percent to about 99 percent, and preferably from about 30 percent to about 95 percent. The porosity measurements are made according to ASTM D-792.

Image-Forming Substances

The image-forming substance may be any aqueous-based, organic-based, or sublimable ink or dye which is useful in the formation of an image and is unaffected by the fusing of the receptive medium.

Nonlimiting examples of inks include those inks generally identified or described in Burachinsky et al, "Inks", Kirk-Othmer *Encyclopedia of Chemical Technology*, Third Ed., Vol. 13, pp. 374-399 (John Wiley & Sons, New York, 1981), the disclosure of which is incorporated by reference. Desirably, classes of inks suitable for the present invention include ballpoint inks, felt-tip inks, luminous inks, disappearing or invisible inks, temperature indicating inks, jet inks, and any of the classes of printing inks. Presently preferred inks are jet inks, e.g., for colored images: "HP" 51606C ink, for black images: "HP" 51606A ink, and for document printing: "HP" 51608A ink. All of these inks are commercially available from Hewlett-Packard Corporation in conjunction with the sale of ink-jet printing apparatuses.

Non-limiting examples of dyes include those dyes generally identified or described in Bannister et al., "Dyes and Dye Intermediates", Kirk-Othmer Encyclopedia of Chemical Technology, Third Ed., Vol. 8, pp. 159-212 (John Wiley & Sons, New York, 1979), the disclosure of which is incorporated by reference. Desirably, classes of dyes include aniline (basic) dyes.

Nonlimiting examples of the aqueous-based solvents and organic-based solvents and suspending liquids may be found in the "Inks" article identified above or in Wannamacher et al., "Dye Carriers", Kirk-Othmer Encyclopedia of Chemical Technology, Third Ed., Vol. 8, pp. 151-158 (John Wiley & Sons, New York, 1979), the disclosure of which is incorporated by reference herein. Classes of aqueous-based solvents desirable for use in the present invention include solutions of water and glycols, such as ethylene and propylene glycol. Useful organic-based solvents include toluene and butanol. The presently preferred solvent is believed to be an ethylene glycol/water solution used with the "HP" 51606C and 51606A inks, commercially available from Hewlett-Packard Corporation.

Loading the Receptive Media with Image-Forming Substances

A hydrophobic receptive medium may be loaded with at least one organic-based or sublimable image-forming substance. A hydrophilic receptive medium may be loaded with at least one aqueous-based, organic-based, or sublimable image-forming substance. In either type of medium, the image-forming substance is loaded into any arrangement of patterns or characters to define and form an image.

The aqueous-based image-forming substance enters the pores of a hydrophilic receptive medium because hydrophilic surfaces of the medium are wet by a aqueous-based solvents used with aqueous-based image-forming substances. The organic-based image-forming substance enters the pores of a hydrophobic or hydrophilic receptive medium because hydrophobic or hydrophilic surfaces are wet by organic-based solvents used with organic-based image-forming substances.

The loading of liquid-based image-forming substances into receptive media may employ any known method of applying the image-forming substance to the surfaces of the receptive medium. If an entire surface may be loaded, nonlimiting examples of loading image-forming substances include wiping, knifing, spraying, rolling, thermally-induced sublimating or other common coating or printing application techniques. If a portion of a surface is used to form an image of characters or patterns, nonlimiting examples of loading image-forming substances include any form of printing, tracing, injecting, silk screening, writing, inscribing, or other common printing application techniques. The presently preferred loading technique employs commercially available ink jet printers, such as a "Paintjet" printer commercially available from Hewlett-Packard Corporation.

Restructuring Receptive Media

With image-forming substances loaded into pores of receptive media, receptive media may be restructured to encapsulate the image-forming substances in the receptive media. The encapsulation is caused by heating the receptive medium at temperatures less than the degradation temperature of the image-forming substance. Desirably, the temperature should not exceed about 140° C. for more than thirty seconds. Preferably, in order to minimize any deleterious change to the image-forming substance loaded into a polyolefin receptive medium, the fusing of the receptive medium should not exceed about 140° C. for more than 5 seconds.

If the preferred polyolefin receptive media having a hydrophilic shell, loaded with image-forming substances, is heated within about two hours after the loading of the image-forming substances, there is no discernable bleeding of the image-forming substances in the pores of the receptive media. Thus, fusing within about two hours after loading minimizes the generation of a distorted image.

If the receptive media is prepared according to the disclosure of U.S. Pat. No. 4,501,293, fusing should occur within one-half hour after fusing to avoid bleeding and distorting the loaded image.

Preferably, the receptive media is restructured by fusing as expeditiously as possible after the receptive media is loaded with image-forming substances.

The pores of the receptive media are closed by the restructuring of the receptive media. The receptive media transforms from a non-transparent appearance to an essentially transparent appearance, except for the image formed therein.

The image-forming substances are encapsulated within the restructured media in the same location(s) as when such image-forming substances were loaded. An encapsulated image is permanently loaded within the restructured medium and can not be changed, modified, or subjected to tampering without noticeable variation to the media. The encapsulated image also is undistorted by any surface interaction of the restructured media with moisture, pressure or other deleterious effect.

Substrates for Receptive Media

Substrates for the receptive media are optional, but desired. A substrate provides temporary or permanent support for the receptive media while the receptive media is being restructured. Substrates may be opaque, translucent, or transparent in appearance, depending on the final appearance desired for the image formed and encapsulated in the receptive media. Nonlimiting examples include a colored or black image in the restructured media laminated to a transparent substrate and a white or contrasting color image in the restructured media laminated to an opaque substrate.

A substrate may be made of any individual or combination of compositions of polymeric, ceramic, cellulosic, glassy, metallic, or carbonaceous materials having a shape that can support temporarily or permanently the shape of the receptive media. Desirably, the substrate is non-porous and polymeric. Nonlimiting examples of non-porous, polymeric substrates include polyethylene terephthalate films, polyethylene films, polyurethane, polypropylene films, cellulose acetate films, or polyimide films.

The substrate may be joined with the receptive media by any means useful. If the joining is to be temporary, the use of a low-tack adhesive is desirable. If the joining is to be permanent, a permanent adhesion is desirable, such as by lamination. Lamination may be performed according to known techniques in the art, such as sonic welding, spot thermal bonding, or adhesion with pressure-sensitive adhesives, hot-melt adhesives, or solvent-borne adhesives.

The relative dimensional size of the substrate to the size of the receptive media is also variable according to the desired appearance after restructuring of the media. For example, if the receptive media is planar and is laminated to a substrate which is also planar, the thickness of the receptive media may be greater or lesser than the thickness of the substrate. A greater thickness for the receptive medium is desired when the medium requires a large volume of image-forming substance to form an image. A smaller thickness for the receptive medium is desired when the medium requires a more substantial support when the medium is restructured. It is presently preferred for the receptive media to have smaller thicknesses than the substrates, e.g., on the order of 15-30% of the thickness of a substrate in order to ease handling during image formation and use.

Preferred Receptive Medium Construction

The presently preferred receptive medium is a hydrophilic porous, supporting structure described in these Embodiments of the Invention which is polymeric and has a complex geometric configuration for loading of aqueous-based image-forming substances. Preferably, the porous, polymeric structure is shaped in the form of a membrane.

Figure 9A:
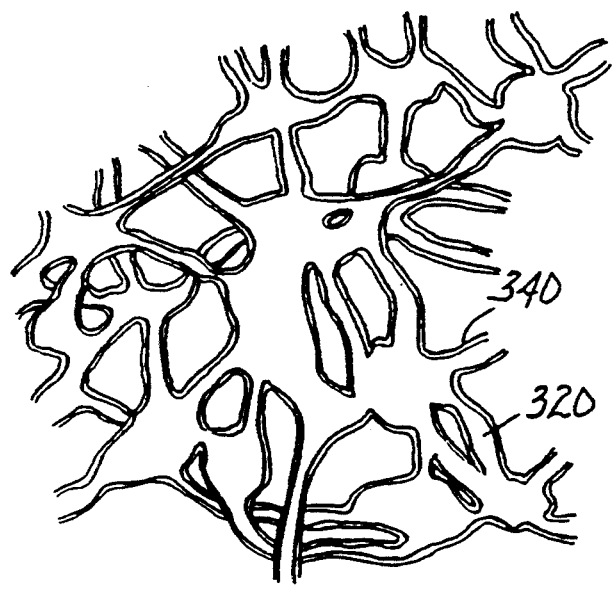
FIG. 9a is an illustration of a receptive medium microstructure having a hydrophilizing shell of poly(vinyl alcohol) enveloping surfaces of the microstructure and a coating of at least one image-forming substance thereon.
Figure 9B:
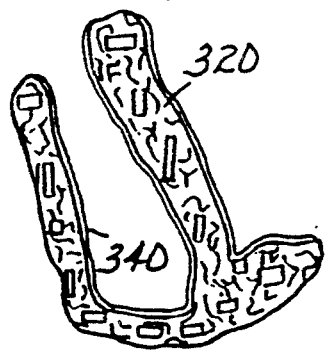
Figure 10:
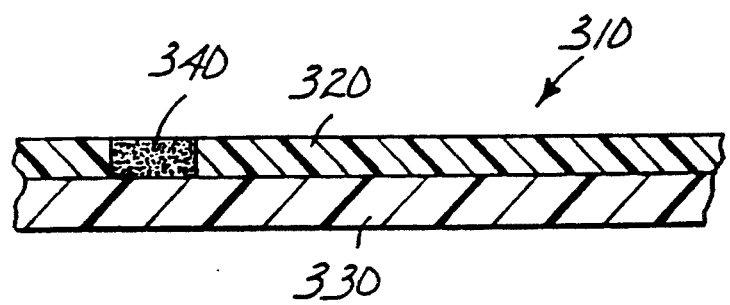
FIG. 10 is a cross sectional view of an non-transparent porous receptive medium laminated to a transparent film substrate having an ink loaded into a location in the medium to form an image.
Figure 11:
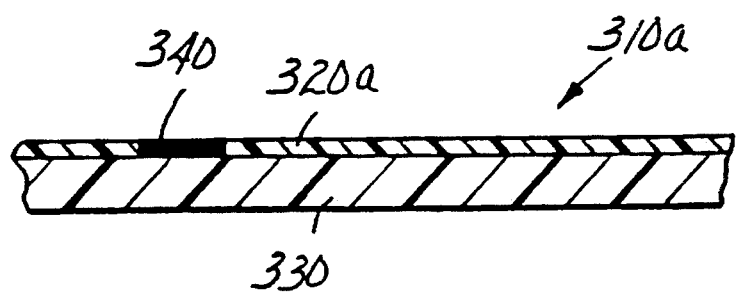
FIG. 11 is a cross sectional view of the laminate of FIG. 10 after heat has restructured the receptive medium encapsulating the ink in the desired location within the medium.

FIGS. 9a and 9b illustrate a receptive medium microstructure. FIGS. 10 and 11 illustrate the cross-sectional effect of encapsulating an image in a receptive medium laminated to a substrate. In FIG. 10, an image forming structure 310 is shown. Structure 310 has a porous, polymeric receptive medium 320 supported by a polymeric substrate 330. At least one location of porous receptive medium 320, an image forming substance 340 is loaded. FIG. 9a illustrates the coverage of image forming substance 340 on the porous reticulated surfaces of medium 320. After heating to restructure porous receptive medium 320, FIG. 11 shows the structure 310a with the image forming substance 340 encapsulated in a restructured receptive medium 320a, with some reduction in size of the thickness of medium 320a due to collapse of the porous structure.

Thus, the permanent and undistorted image can be formed in a planar receptive medium laminated to a planar, transparent substrate to make an overhead transparency that does not need surface treatments such as starch or transparent overlays to protect the image. By choice of at least one image-forming substance loaded into the receptive medium in patterns or characters to form an image, a detailed, multi-colored permanent image for overhead projection may be made.

The permanent and undistorted image can be formed in a planar receptive medium laminated to a planar substrate to make a tamper-resistant identification device. By choice of at least one image-forming substance loaded into the receptive medium in patterns or characters, a tamper-resistant document such as a security card may be formed. The card may be a laminate of the restructured receptive medium, encapsulating the image in a permanent and undistorted manner, and a substrate of opaque, translucent, or transparent appearance.

A specific, but nonlimiting example of the formation of an identification document such as a security card having a permanent and undistorted image is the use of receptive media as a signature space on the card. The loading of the ink is accomplished by handwriting a signature. The receptive medium is restructured to encapsulate the image of the signature within the receptive medium. The image is made permanent within the signature space and is undistorted from the original signature loading of the ink.

Nonlimiting examples of other uses of the receptive media to form permanent and undistorted images include the formation of detailed maps laminated to an opaque substrate, the formation of markers or signs laminated to translucent substrates for back-lit information displays, or fine art.

Oxygen Scavengers

Hydrophilic porous supporting structures have considerable usage as reservoirs for enzyme systems. The enzyme system in a water-miscible solvent system is typically loaded on the surfaces of the hydrophilic shell of the porous supporting structure throughout the complex geometric configuration of the porous supporting structure.

The supporting structure may be composed of any individual or combination of supporting structures described in these Embodiments of the Invention and which are polymeric, ceramic, cellulosic, glassy, metallic, or carbonaceous porous materials. These porous materials may be either hydrophobic or hydrophilic in nature.

Enzyme Systems

Nonlimiting examples of enzyme systems include glucose oxidase; a glucose/glucose oxidase combination; a glucose oxidase/sucrose combination; a starch/amylase/glucose oxidase combination; a cellulose/cellulase/glucose oxidase combination; a milk powder/lactase/glucose oxidase combination;a glucose oxidase/fructose isomerase/fructose combination; a glucose oxidase/lactase/whey solids/lactose combination; a glucose/lactase/lactose combination; a glucose oxidase/maltase/starch combination; a glucose oxidase/maltase/maltose combination; a mushroom tyrosinase/tyrosine combination; a glucose oxidase/sucrose/sucrase combination; and any combination of Ebden-Meyerhoff-Citric Acid cycle enzymes.

Typically the enzyme system is processed in a water-miscible solvent system, such as an aqueous buffer system. The water-miscible solvent wets the hydrophilic surfaces of the porous supporting structure and delivers the enzyme system to all available surfaces of the hydrophilic porous supporting structure.

Of the preceding illustrative examples, a 50% (W/V) dextrose/citrate buffer solution (having a pH of 6.3) containing glucose oxidase enzyme in a concentration of 2.5. mg/ml and having a "Finnsugar stated activity" of 110 units/mg is presently preferred for loading on a hydrophilic porous supporting structure. "Finnsugar stated activity" is determined by AP0002, Revision F of Glucose oxidase, titrimetric assay published in 1988 by Finnsugar Biochemicals, Inc. of Schaumberg, Ill., the disclosure of which is incorporated by reference herein.

Nonlimiting examples of loading the enzyme system onto the hydrophilic porous supporting structure include soaking, wiping, dipping, rolling, spraying, or knifing. Drying at ambient temperatures and pressures or slightly elevated temperatures not exceeding approximately 70° C. permits the evaporation of the water-miscible solvent system without deleteriously affecting or inactivating the enzyme loaded on the surfaces of the hydrophilic porous structure. Alternatively, drying may occur at higher temperatures if there is a highly convective air flow about the porous supporting structure.

Enzyme-loaded Hydrophilic Porous Supporting Structures

As seen in FIG. 12a, the hydrophilic membrane 410 has a layer of enzyme system 420 loaded on the poly(vinyl alcohol) shell enveloping the complex geometric configuration of the porous supporting structure. The layer of enzyme system is loaded on all available hydrophilic surfaces of the porous supporting structure because the hydrophilic shell permits the wetting of such surfaces by a water-miscible solvent system containing the enzyme system.

The layer 420 of enzyme system forms, without a binder needed, on the hydrophilic surfaces of the membrane 410 as the water-miscible solvent evaporates. The thickness of the layer must be at least a minimally useful thickness. Because the hydrophilic shell does not denature the enzyme system, substantially all of the enzyme system forming a layer remains active for oxygen scavenging.

Desirably, the layer 420 of enzyme system is sufficiently thin to avoid blocking, clogging, or skinning the pores of the supporting structure. Thus, for a porous structure having a pore size of about an average of 0.5 $\mu$m, the layer 420 of enzyme system does not exceed about 0.075 $\mu$m.

Preferably, the porous supporting structure does not lose more than about 60% of its pore size due to the formation of the hydrophilic shell and the loading of the enzymatically active material thereon. Thus, for a porous supporting structure having a pore size of an average of 0.5 $\mu$m, the layer 420 of enzyme system does not exceed about 0.15 $\mu$m in thickness. As seen in FIG. 12a, the layer 420 is illustrated as having the presently preferred thickness relative to the monolayer thickness of the hydrophilic membrane 410 and the pore size shown.

The enzyme system protects oxygen sensitive products from deleterious interaction with molecular oxygen, whether the molecular oxygen is in the headspace of a container at the time of packaging or enters the packaging thereafter. Even within an enclosed area, an oxygen sensitive product may have a limited shelf life due to its reactivity with oxygen in the headspace of the container.

Nonlimiting examples of oxygen sensitive products which may be protected by the present invention include natural and processed food products such as cheese, luncheon meats, bacon, fermented dairy products, fruits and vegetables, raw meats, poultry, fresh and salted fish, intermediate moisture foods (such as jerky, pet foods, and granola bars), high fat moist bakery products, acidified dairy products, mayonnaise and salad dressings, controlled atmosphere/modified atmosphere refrigerated extended shelf life foods (such as partially cooked meals, pasta dishes, sauces, cut fruit, and vegetable salads, and other water-bearing foods.

Because the enzyme system is loaded on all available surfaces of the hydrophilic porous structure, and because water or moisture may penetrate the hydrophilic porous structure, an enzyme-catalyzed reaction may occur throughout the porous structure. The enzyme-loaded porous structure need not necessarily be in contact with an oxygen sensitive product. Thus, the enzyme-loaded porous structure may be a liner or pad, either inside the cap or lid at the top of the headspace of a container or along any portion of the interior of the package within or beyond contact with the oxygen sensitive product.

The oxygen sensitive product may be enclosed in a package with the enzyme-loaded hydrophilic porous structure within the package. Molecular oxygen, both remaining in the package at the time of packaging and entering the package after packaging is scavenged by operation of the enzyme system. The enzyme catalyzed reaction of a substrate, oxygen, and if necessary, water forms byproducts and consumes oxygen. With the porosity of the supporting structure substantially retained, the flow of oxygen and water or moisture within the package may pass through the enzyme-loaded, porous supporting structure.

If the enzyme system includes the substrate, the enzyme-catalyzed reaction can occur at all available surfaces of the structure. Because water readily penetrates the hydrophilic porous structure, vastly more interior surface area is available for the oxygen consuming reaction than just at the exterior surfaces of the structure.

The form of the porous structure is not limited to liners or pads but may take any of the forms described above. When loaded with an enzyme system, any of those forms may be used for oxygen scavenging.

So long as the oxygen sensitive product is not adversely affected by the presence of a substrate or reaction byproducts in the package, the product's shelf life is improved by the consumption of oxygen before reaction with the oxygen sensitive product.

Some catalyzed reactions may generate hydrogen peroxide as a byproduct. The released hydrogen peroxide may be of some benefit to extend shelf life of meats, poultry and fish if the hydrogen peroxide is in direct contact with the wet surfaces of those foods. Alternatively, concern about the generation of hydrogen peroxide may be minimized by including catalase in the enzyme system. The catalase converts hydrogen peroxide into water and oxygen, which are further reacted with substrate in the presence of the enzyme until the cycle effectively consumes oxygen in the package from all sources.

While a planar surface not having a complex geometric configuration may have a layer of the enzyme system placed thereon and perform an oxygen scavenging function within a package, the surface area available for immobilizing the enzyme system and for providing reactive sites for oxygen scavenging is much more limited. For example, monolayer coverage of an enzyme system on a non-porous structure provides only about 0.1 $\mu g/cm^2$ of enzyme, whereas adequate enzyme coverage for practical oxygen scavenging requires a minimum of about 3 $\mu g/cm^2$ of enzyme. Thus, it is not possible to achieve a practical oxygen consumption using an enzyme system on a flat film.

However, a porous supporting structure having a complex geometric configuration does achieve adequate oxygen scavenging because of the extremely large surface area/exterior surface area ratio. For example, a 100 $\mu m$ thick membrane having a 20 $m^2/gm^2$ surface area provides about 600 times the surface area as one side of a 1 $cm^2$ surface of a flat film. Thus, a porous supporting structure having a complex geometric configuration can have at least 600 times as much enzyme system loaded on its porous surfaces.

Other materials may be added to a package containing the enzyme-loaded porous structure of the present invention. Nonlimiting examples include adding a second material having additional amounts of the same or a different substrate into the package, preferably in a contiguous position to the enzyme-loaded porous structure. In general, because the enzyme is a catalyst and the substrate is converted to a byproduct in the oxygen scavenging process, the greater the amount of substrate in the package, the greater the amount of oxygen which may be consumed.

This invention is not limited to the embodiments described here or by the examples which follow.

EXAMPLES

In the examples to follow, certain tests were conducted and are described below:

Gurley Value—This value is a measurement of time in seconds to pass 50 $cm^3$ of air through a porous film according to ASTM D-726, Method A.

Bubble Point Pore Size—This is a measurement of the maximum effective pore size, in microns, according to ASTM F-316. This value is also referred to as "pore size" in the Examples.

Porosity—This is a measure of the void volume of the porous article, and is derived from the measurement of specific gravity of the article, according to ASTM D-792. The porosity is defined as:

$$\text{Porosity} = \left(1 - \frac{\text{bulk density}}{\text{polymer density}}\right) \times 100$$

Tensile strength—Values measured according to ASTM D 638-80 using an Instron model 1122 tensile tester under the following conditions:

| Jaw Gap: | 5.08 cm |
|---|---|
| Jaw Speed: | 50.8 cm/min |
| Sample Size: | 2.54 cm wide strip |

MD and TD values for the tensile strength refer to measurements made in the "machine direction" and the "transverse direction" respectively.

Water Permeability—Water permeability was determined by placing a 74 mm diameter piece of the membrane in a test cell, which used an o-ring to seal the membrane to a sintered stainless steel back-up plate. The cell was equipped with a 350 ml water reservoir and was pressured with compressed nitrogen. The water flow rate was calculated by measuring the volume of water passed through the sample in a given time, with a 10 psi (or 68,947 $N/m^2$) head pressure. At least three measurements were averaged for each permeability value reported.

Example 1

Preparation of the poly(vinyl alcohol) precursor, syndiotactic poly(vinyl trifluoroacetate), was performed in a one gallon glass bowl jacketed pressure reactor having a stainless steel lid fitted with a metal turbine agitator blade on a sealed shaft, two mixing vanes, a thermowell and at least two valved openings. The system was purged with a sweep of dried argon to remove moisture and oxygen before adding reactants or solvent. Materials were weighed and transferred in closed vessels under inert gas and anhydrous conditions. Charges were made through rubber septa covering the opened valves in the reactor lid using proper techniques to prevent uptake of atmospheric moisture and oxygen. Into the reactor were placed, in order, 3025 g of Freon 113, 17.5 ml of a premix containing 2.5 g of trifluoroacetic anhydride in 25 ml of Freon 113, 355 g vinyl trifluoroacetate monomer, 14 ml of a second premix containing 2.5 g of bis(4-t-butylcyclohexyl) peroxydicarbonate (commercially available as "Percadox" 16N from Akzo Chemie America, Noury Chemicals of Chicago, Ill.) in 25 ml of Freon 113. The reactor temperature was raised to 45° C. and maintained at that temperature for about 18 hours with an agitator speed at about 1000 rpm. A slight exotherm was observed during the reaction with a maximum system pressure of about 10–12 psig (0.7–0.8 $kg/cm^2$). The polymerized, syndiotactic poly(vinyl trifluoroacetate) (PVTFA) was isolated by filtration and dried at 40° C. under vacuum overnight.

A microporous polyethylene (PE) membrane, made by thermally induced phase separation as disclosed in Example 23 of U.S. Pat. No. 4,539,256 (Shipman) the disclosure of which is incorporated herein by reference, having a maximum pore size of 0.5 micron, a porosity of 81.5 percent and a thickness of 0.074 mm, was saturation treated with a 4 percent (w/v) acetone solution of PVTFA using an extrusion die. The membrane was dried slowly for 1.6 minutes in a two zone air floatation oven with the two zones set at temperatures of 27° C. and 38° C. respectively, resulting in a 22.2 weight percent add on of the PVTFA shell formed on the external and internal pore surfaces. No substantial blocking of the pores occurred, nor was a PVTFA skin formed on the covered side as evidenced from scanning electron microscopy (SEM) analysis. The complex geometric configuration of the membrane was substantially retained. Bubble point measurements showed a reduction in the maximum pore size to 0.44 micron.

the final PVA shell hydrophilic membrane are reported in Table 1 below.

TABLE 1

| Membrane | Coating Weight | Thickness | Pore Size | Percent Pore size Loss | Porosity | Gurley | Water Permeability* |
|---|---|---|---|---|---|---|---|
| PE | — | 0.074 mm | 0.496 μ | — | 81.5% | 9.4 sec | 0** |
| PVTFA covered PE | 22.2% | 0.056 mm | 0.438 μ | 12% | 73.2% | 17.6 sec | 0** |
| PVA shelled PE | 8.4% | 0.056 mm | 0.463 μ | 7% | 73.6% | 15.2 sec | 0.052 L/ (m$^2$*hr*Pascals) |

*Water permeability measured at 68,930 Pascals (10 psi).
**No flow of water occurs at 68,930 Pascals through this hydrophobic membrane without an ethanol pre-wetting step due to the hydrophobicity of PE and PVTFA. When measured after ethanol pre-wetting and a solvent exchange of water, PE Water Permeability measured 0.043 and PVTFA coated PE Water Permeability measured 0.033 L/(m$^2$*hr*Pascal), respectively.

A piece of this dry membrane was placed in an ammonia-saturated glass vessel for 2 minutes in order to convert, in-situ, the PVTFA shell to a poly(vinyl alcohol) (PVA) shell. The ammonia atmosphere was generated by placing a concentrated ammonium hydroxide solution in the bottom of the vessel. A 68 weight percent reduction in the weight of the shell resulted from the hydrolysis reaction.

Fourier Transform Infrared, (FT-IR), spectroscopy (at 4 cm$^{-1}$ resolution, 64 scans, between a range of 4000 cm$^{-1}$ and 400 cm$^{-1}$, through the membrane) confirmed that the 68 weight percent loss in shell weight, which occurred during this basic hydrolysis reaction step was due to the quantitative loss of the trifluoroacetate group from the PVTFA. This amount of weight loss corresponded exactly to the amount of weight loss expected for 100% conversion from: PVTFA to PVA. Upon removing the membrane from the ammonia atmosphere, it displayed spontaneous and nearly instantaneous wetting with water. The complex geometric configuration of the membrane was substantially retained throughout the hydrolysis treatment as was evidenced by a pore size loss of less than eight percent.

The ability of the hydrophilic membrane to resist wash-out of the PVA shell by common organic solvents was demonstrated by soaking pieces of the membrane in large amounts of acetone, isopropyl alcohol, and 1,1,1-trichloroethane. After 45 minutes of soaking in each of these solvents, the re-dried membranes retained their hydrophilicity, as shown by their spontaneous and nearly instantaneous wetting with water. The ability of the hydrophilic membrane to resist wash-out of the PVA shell by water was demonstrated by passing 2000 ml of deionized water through a 36 cm$^2$ piece of this membrane. After drying, the hydrophilicity of the membrane remained unchanged (i.e., it was spontaneously and nearly instantly wetted with water).

The porous properties of the starting PE microporous membrane, the PVTFA covered membrane, and

Example 2

A hydrophilic membrane was prepared according to the procedure of Example 1 except that the syndiotactic PVTFA solution was applied to the membrane using a #8 wire-wound bar to spread the PVTFA solution on the membrane. The sample was allowed to dry at room temperature in a ventilation hood to produce a PVTFA treated membrane without causing pore blockage or PVTFA skin formation as shown by SEM examination. The PVTFA treated membrane retained the complex geometric configuration of the starting membrane. The sample was reacted with vaporous ammonia as in Example 1 to yield a hydrophilic membrane, as shown by its spontaneous and nearly instantaneous wetting with water.

Example 3

Table 2 below provides data on mechanical properties of unprocessed hydrophobic microporous membranes and the hydrophilic microporous membranes of the present invention, both before and after in-situ conversion to the corresponding PVA shell membrane. The base PE membrane was the same as that used in Example 1. The PVTFA treated membranes were prepared according to the procedure detailed in Example 2, using various concentrations of syndiotactic PVTFA solutions in acetone as noted in Table 2 below. Hydrolysis of the PVTFA treated membranes was performed in an ammonia atmosphere as in Example 1. The PVTFA add-on was determined by weight difference after a piece of the PVTFA treated membrane had been extracted with acetone to a constant weight. The weight percent of PVA was calculated from the weight percent PVTFA above, assuming 100 percent conversion to PVA. Tensile measurements were performed on 2.54 cm wide strips of membrane as described above. Tensile strength is defined as the Newtons/m$^2$ at break normalized to the cross-sectional area.

TABLE 2

| Example | Membrane Description Solution Concentration | Weight Percent PVTFA or PVA Add on | Tensile Strength At Break ((Newtons/m$^2$) × 10$^6$) | | Elongation To Break (%) | |
|---|---|---|---|---|---|---|
| | | | MD | TD | MD | TD |
| 3A | Uncoated PE from Ex. 1 | — | 5.76 | 0.32 | 47 | 107 |
| 3B | Ex. "3A" covered with 4% PVTFA | 29.2 | 9.33 | 5.79 | 38 | 53 |
| 3C | Ex. "3B" after conversion to PVA | 9.3 | 10.13 | 6.64 | 66 | 118 |
| 3D | Ex. "3A" covered with 6% PVTFA | 36.1 | 9.82 | 6.40 | 28 | 46 |
| 3E | Ex. "3D" after conversion to PVA | 11.6 | 10.43 | 7.34 | 43 | 97 |
| 3F | Ex. "3A" covered with 8% PVTFA | 42.0 | 9.88 | 6.55 | 20 | 45 |

TABLE 2-continued

| Example | Membrane Description Solution Concentration | Weight Percent PVTFA or PVA Add on | Tensile Strength At Break ((Newtons/m$^2$) × 10$^6$) | | Elongation To Break (%) | |
|---|---|---|---|---|---|---|
| | | | MD | TD | MD | TD |
| 3G | Ex. "3F" after conversion to PVA | 13.4 | 11.62 | 7.97 | 50 | 91 |

Example 4

A microporous PE membrane, prepared according to Example 23 of U.S. Pat. No. 4,539,256 (Shipman), having 0.26 micron pore size and a 77 percent porosity was treated with a 4 percent (w/v) solution of syndiotactic PVTFA (prepared according to Example 1) in cyclohexanone. The web was passed through an immersion trough containing the tactic PVTFA solution, which was heated to 46° C. to decrease its viscosity, then passed through a rubber nip station to squeeze off excess solution, and dried in an air floatation oven at a temperature of 40.5° C. to produce a PVTFA treated membrane. Control of the PVTFA add-on was more difficult using this method, and the membrane had a tendency to stretch as it passed through the nip roll station. After hydrolysis with ammonia vapor, as in Example 1, the membrane was hydrophilic as shown by its spontaneous and nearly instantaneous wetting with water.

Example 5

A microporous polypropylene (PP) membrane, made according to the procedure of Example 9 of U.S. Pat. No. 4,726,989 (Mrozinski), the disclosure of which is incorporated herein by reference, was treated with a 4 percent (w/v) acetone solution of syndiotactic PVTFA following the procedure of Example 2. Upon hydrolysis with ammonia vapor as in Example 2, the membrane was hydrophilic, as demonstrated by its spontaneous and nearly instantaneous wetting with water. The porous properties of the starting PP membrane and the hydrophilic membrane of the present invention are shown in Table 3. Pore size loss was less than 11 percent, demonstrating a substantial retention of the physical structure of the membrane while imparting hydrophilicity to the membrane surfaces.

Example 6

A 0.023 mm thick PP microporous membrane, prepared according to Example 9 of U.S. Pat. No. 4,726,989, having a 0.2 micron pore size, a 66.7 percent porosity, and a Gurley value of 25.6 sec, was treated with PVTFA according to the procedure of Example 2, using a 2 percent (w/v) solution of syndiotactic PVTFA in acetone followed by in-situ NH$_3$ hydrolysis. The treatment/hydrolysis operation was repeated three times to prepare the hydrophilic membrane of the present invention. The resulting hydrophilic membrane was instantaneously wet with water. The ability of the PVA shell to resist wash-out by water was demonstrated by placing the membrane in boiling water for 5 hours, drying the membrane, and demonstrating that the membrane was still spontaneously and nearly instantaneously wet with water, even though there was a 1.8 percent reduction in the membrane's weight during the exposure to boiling water.

Example 7

The syndiotactic PVTFA treated membrane of Example 1 was placed in a stream of anhydrous NH$_3$ for 2 seconds. The NH$_3$ stream was directed against the membrane so as to force the ammonia through the pores of the membrane. After this dry ammonolysis treatment, the hydrophilicity of the membrane was comparable to the hydrophilicity of the membrane of Example 1, as shown by spontaneous and nearly instantaneous wetting with water. FT-IR showed that 100 percent conversion of the PVTFA to PVA was accomplished. This demonstrated that the 2 minute ammonolysis time of Example 1 was only required in order to allow the NH$_3$ vapor to diffuse into the pores, and that by forcing the NH$_3$ into the pores, the true ease of conversion to PVA is appreciated.

Example 8

The ability to convert syndiotactic PVTFA treated membranes into PVA shell membranes using a variety of hydrolysis reagents and conditions was demonstrated by dipping the PVTFA treated membrane of Example 1 into solutions of various bases as well as a HCl solution. The results are shown in Table 4.

TABLE 3

| Sample | Weight Percent PVA Add-On | Thickness | Pore Size | Percent Pore Size Loss | Porosity | Gurley | Water Permeability* |
|---|---|---|---|---|---|---|---|
| PP | — | 0.081 mm | 0.974 μ | — | 82.9% | 3.3 sec | 0** |
| PVA shelled PP | 10.2% | 0.076 mm | 0.874 μ | 11% | 79.2% | 3.7 sec | 0.15 L/(m$^2$*hr*Pascals) |

*Water permeability measured at 68,930 Pascals.
**No flow of water occurs at 68,930 Pascals through this hydrophobic membrane without an ethanol pre-wetting step due to the hydrophobicity of PP. When measured after ethanol pre-wetting and a solvent exchange of water, PP water permeability measured 0.13 L/(m$^2$*hr*Pascals).

TABLE 4

| Example | Hydrolysis | pH | Immersion Time | Result |
|---|---|---|---|---|
| Comparison 8A | 0.5M HCl in MeOH | <2 | 30 min | not hydrophilic |
| 8B | 0.1M NaOH in MeOH | 13 | 30 min | hydrophilic |
| 8C | 0.1M Na$_2$CO$_3$ in 50:50. MeOH:H$_2$O | — | 30 min | hydrophilic |

TABLE 4-continued

| Example | Hydrolysis | pH | Immersion Time | Result |
|---|---|---|---|---|
| 8D | 10% conc. NH₄OH in MeOH | 8 | 30 min | hydrophilic |
| 8E | 0.1M KOH in H₂O | 13 | 30 min | outside surface hydrophilic |
| 8F | 0.1M KOH in H₂O | 13 | 4 days | outside surface hydrophilic |

In order to effect the conversion of PVTFA to PVA throughout the membrane, the solution must be able to wet the PVTFA treated membrane, or the base must be volatile in order to deliver the hydrolysis reagent to the internal pore surfaces (c.f. Examples 10E and 10F). The 30 minute immersion time was probably excessive, but was chosen to ensure complete hydrolysis. All cases that resulted in a hydrophilic membrane (Examples 10B, 10C and 10D) showed 100 percent conversion of the PVTFA to PVA under FT-IR analysis performed according to Example 1.

Example 9

The PE microporous base membrane of Example 1 was treated, as in Example 2, with 4 percent (w/v) syndiotactic PVTFA solutions in various solvents as noted in the Table 5 below. This example demonstrates that a variety of solvents other than the preferred acetone, including: esters, cyclic ethers, aliphatic and aromatic ketones, nitriles, and amides, can be used to prepare PVTFA treated membranes. Also, shown by comparison, are solvents which could not be made to work, due to the substantial insolubility of PVTFA in these solvents. Copolymers of PVTFA, described in other examples within this disclosure, are not limited to the solvents listed below.

TABLE 5

| Example | Solvent | Coating Conditions | Result |
|---|---|---|---|
| 9A | Ethyl Acetate | Room Temp. (21° C.) | hydrophilic |
| 9B | Tetrahydrofuran | 40° C. on PE | hydrophilic |
| 9C | Dimethyl Formamide | Room Temp. (21° C.) | hydrophilic |
| 9D | Acetophenone | 80° C. on PP | hydrophilic |
| 9E | Acetonitrile | Room Temp. (21° C.) | hydrophilic |
| Comparison 9F | Diethyl Ether | — | PVTFA not substantially soluable |
| Comparison 9G | 1,1,1-Trichloroethane | — | PVTFA not substantially soluable |
| Comparison 9H | Aliphatic Alcohols (i-PA, EthOH, n-PA, n-BuOH) | — | PVTFA not substantially soluable |
| Comparison 9I | Trifluoroacetic Acid | — | PVTFA not substantially soluable |
| Comparison 9J | 1,1,1-Trifluoroethanol | — | PVTFA not substantially soluable |

Example 10

Microporous PE membrane samples, prepared according to Example 23 of U.S. Pat. No. 4,539,256, having a pore size of 0.548μ, a thickness of 0.056 mm, a porosity of 88 percent, and a Gurley value of 5.4 sec, were treated, as in Example 2, with 4 percent (w/v) acetone solution of syndiotactic PVTFA copolymers having either vinyl acetate or maleic anhydride as the comonomer. The copolymers were prepared by free radical polymerization of the appropriate ratio of vinyl trifluoroacetate and the corresponding vinyl comonomer (i.e., vinyl acetate or maleic anhydride, respectively) according to Examples 1 and 4, respectively, of U.S. Pat. No. 4,618,649 (Ofstead), which is incorporated herein by reference. In-situ hydrolysis of these treated membranes produced PVA shell membranes which were hydrophilic as evidenced by spontaneous and nearly instantaneous wetting with water. In order to show that the crystallinity of the hydrophilic PVA shell was not excessively disrupted by the incorporation of less than about 5 percent of comonomer, each PVA shell membrane sample was subjected to a water extraction to determine PVA loss. Initial PVTFA and PVA add-ons were determined according to the procedures of Example 3. One liter of water was passed through a disc of each PVA shell membrane having a surface area of 36.3 cm² and the resulting PVA weight loss calculated by weight differential of the membrane sample. The weight loss results tabulated in Table 6 show that less than 1 weight percent of the membrane weight was lost due to the water wash step. The hydrophilicity of the washed and dried samples were comparable to the hydrophilicity of the unwashed membranes, demonstrating that the presence of less than about 5% comonomer had not significantly disrupted the crystallinity of the PVA.

TABLE 6

| Example | Copolymer | | % Weight Add-On | Loss* |
|---|---|---|---|---|
| 10A | PVTFA-co-MA | (99.7/0.3) | 12.2 | −0.25 |
| 10B | PVTFA-co-MA | (99.9/0.1) | 8.5 | −0.05 |
| 10C | PVTFA-co-MA | (99.95/0.05) | 10.1 | −0.10 |
| 10D | PVTFA-co-VA | (96.0/4.0) | 9.5 | 0.85 |
| 10E | PVTFA-co-VA | (98.5/1.5) | 9.2 | 0.30 |

*Negative weight loss indicates a net weight gain. Even though care was taken to use prefiltered water for the flushing, some particulate matter may have collected on the membrane, or these numbers may simply reflect the inherent imprecision of the weight measurement. In any case there was a negligible weight loss due to flushing these samples with water.

Example 11

A microporous polysulfone membrane having a surfactant coating to render it hydrophilic and having a rated 0.45 micron pore size (obtained from Schleicher & Schuell) was rinsed in isopropyl alcohol to remove the surfactant coating. The then hydrophobic polysulfone membrane was saturation-treated with a 4 percent (w/v) solution of syndiotactic PVTFA in acetophenone (a poor solvent for polysulfone) following the procedure of Example 2. The resulting PVTFA treated membrane was hydrolyzed in an ammonia atmosphere according to the procedure of Example 2 to produce a hydrophilic PVA shell membrane which was spontaneously and nearly instantaneously wet with water.

Example 12

A microporous polyvinylidene fluoride, PVDF, membrane made according to Example 22 of U.S. Pat. No. 4,539,256, having a 0.21 micron pore size, a 72 sec Gurley value and a 58.3 percent porosity, was saturation-treated with a 4 percent (w/v) solution of syndiotactic PVTFA by forcing the solution through the membrane by applying a partial vacuum to the opposite side of the membrane. The resulting PVTFA treated membrane was hydrolyzed in an ammonia atmosphere according to the procedure of Example 2 to produce a hydrophilic membrane that was spontaneously and nearly instantaneously wet with water.

Example 13

Polyethylene microporous membranes, prepared according to Example 23 of U.S. Pat. No. 4,539,256, having a range of porosities and pore sizes, were treated with a 4 percent (w/v) solution of syndiotactic PVTFA in acetone according to the procedure of Example 1. Upon hydrolysis with the ammonia vapor according to the procedure of Example 2, hydrophilic PVA shell membranes which were spontaneously and nearly instantaneously wet with water were produced. The porosity, pore size and Gurley values of both the starting membranes, numbers 13A, 13C, 13E, and 13G, and the PVA shell membranes, numbers 13B, 13D, 13F, and 13H, are tabulated in Table 7, along with comments concerning the amount of surface pore blockage that occurred. The extensive pore blockage noted with the 0.101 μm pore size membrane is due to the fact that the solution evaporates more rapidly than it can penetrate into the small pores which results in the formation of a pore-blocking skin at the surface of the membrane. Solvents having lower vapor pressures and/or lower viscosity solutions should lessen the occurrence of this type of pore-blocking skin formation.

TABLE 7

| Sample # | Porosity (%) | Pore Size (μm) | Pore Size Loss (%) | Gurley (secs) | Comments |
| --- | --- | --- | --- | --- | --- |
| 13A | 82.2% | 0.479 | — | 9.9 | |
| 13B | 76.3% | 0.427 | 12% | 12.6 | No pore blockage |
| 13C | 78.5% | 0.213 | — | 29.0 | |
| 13D | 74.5% | 0.098 | 54% | 121.0 | Some pore blockage |
| 13E | 76.3% | 0.149 | — | 53.4 | |
| 13F | 68.9% | 0.102 | 33% | 184.3 | Some pore blockage |
| 13G | 57.8% | 0.101 | — | 269.7 | |
| 13H | 47.5% | <<0.1 | −100% | >>1 K | Complete pore blockage |

Example 14

The procedure of Example 1 was used to prepare a hydrophilic PVA shell membrane from a microporous PE membrane having a pore size of 0.259 microns and a 77 percent porosity, prepared according to Example 23 of U.S. Pat. No. 4,539,256, except that a 4.7 percent (w/v) solution of syndiotactic PVTFA in cyclohexanone was used, and the two zones of the oven were set to 38° C. and 106° C. respectively. The higher viscosity of the cyclohexanone PVTFA solutions relative to the viscosity of the acetone PVTFA solutions coupled with the relatively high oven temperatures used to dry the treated membranes resulted in the formation of an integral pore-blocking skin on the membrane surface. The presence of the skin was demonstrated by an effectively infinite Gurley air permeability value and by SEM analysis.

Example 15

Samples of hydrophilic microporous membranes were prepared according to Example 1 and were subjected to extractions by highly polar organic solvents to demonstrate the ability of the PVA shell to resist washout. The initial PVA add-on was 9.1 weight percent of the untreated hydrophobic microporous membrane. The samples were weighed and then soaked for 1.5 hours in the indicated solvents, followed by four rinses of water to remove the solvent. The samples were dried, reweighed and a percentage weight loss for the hydrophilic membrane calculated by weight differential.

Samples exposed to each of the above solvents remained hydrophilic to varying degrees. Dimethyl formamide (DMF) caused the greatest percentage weight loss of the PVA shell, perhaps because the DMF dissolves the PVA crystallites (c.f. FIG. 3). Thus, while the hydrophilic polymeric structure produced according to the present invention is resistant to washout by DMF at least after continuous exposure for up to 1.5 hours, care should be taken to select a polymeric structure which does not also degrade or dissolve during exposure to the highly polar solvent.

TABLE 8

| Example | Solvent | Sample Percent Weight Loss | Polyvinyl Alcohol Shell Percent Weight Loss |
| --- | --- | --- | --- |
| 15A | Dimethylsulfoxide [DMSO] | 0.7 | 8.0 |
| 15B | Dimethylformamide [DMF] | 3.7 | 40.5 |
| 15C | Glycerol [GLY] | 0.5 | 5.5 |
| 15D | Ethylene Glycol [EtGLY] | 0.2 | 2.2 |

Example 16

An inherently hydrophilic microporous Nylon 6,6 membrane, rated with a 0.45 micron pore size, obtained from Schleicher & Schuell of Keene, N.H., was saturation-covered with a 4 percent w/v acetone solution of syndiotactic PVTFA following the procedure of Example 2. The resulting PVTFA envelopment of the internal and external surfaces of the membrane did not block the pores, but due to the hydrophobicity of PVTFA, the Nylon 6,6 membrane was rendered hydrophobic. Upon reaction with the ammonia vapor of ammonium hydroxide, as in Example 2, the PVA shell membrane again became hydrophilic as demonstrated by spontaneous and nearly instantaneous wetting with water. Characterization data, before and after this treatment are tabulated in Table 9, below. This example demonstrated the use of the present treatment to provide hydroxyl functional groups to the surface of a hydrophilic membrane without significantly blocking the pores or reducing the hydrophilicity.

TABLE 9

| Example | Condition | Pore Size | Pore Size Loss | Gurley | Porosity |
|---------|-----------|-----------|----------------|--------|----------|
| 16A | Uncovered | 0.771 μ | — | 14 sec | 61.7% |
| 16B | PVA Shell | 0.740 μ | 5% | 24 sec | 60.4% |

Example 17

A piece of Gore-Tex ™ poly(tetrafluoroethylene) membrane, manufactured by W. L. Gore and Associates, Inc. of Elkton, Md. was saturated with a 5 percent w/v acetone solution of syndiotactic PVTFA prepared according to Example 1 using a #14 wire-wound bar to spread the solution. This sample was allowed to dry at room temperature in a ventilation hood to produce a PVTFA shell on the external and internal surfaces of the membrane, without causing pore blockage or PVTFA skin formation, as shown by SEM examination. The sample was reacted with vaporous ammonia as in Example 1 to yield a highly hydrophilic membrane, as shown by being spontaneously and nearly instantaneously wetted with water.

Example 18

A piece of a calendered spunbonded PE web, commercially available under the trademark "Tyvek T-984", from E. I. DuPont of Wilmington, Del., having an average Gurley air flow of 3.1 sec per 50 cm$^3$ of air, was saturation-covered with a 4 percent w/v acetone solution of syndiotactic PVTFA according to the procedure of Example 2. After drying and reacting in-situ with ammonia vapor, the PVA shell web was hydrophilic as judged by being spontaneous and nearly instant wettability with water. The web was still through-porous, since water would pass through the web after the hydrophilization and exhibited a Gurley value of 9.8 sec per 50 cc of air.

Example 19

A polypropylene melt-blown web, was made according to the procedure described in Wente, Van A., "Superfine Thermoplastic Fibers" in Engineering Chemistry, Vol. 48, p. 1342 et. seq. (1956), or in Report No. 4364 of the Naval Research Laboratories, published May 25, 1954, entitled "Manufacture of Superfine Organic Fibers" by Wente, V. A.; Boone, C. D.; and Fluharry, E. L., the disclosures of which are incorporated by reference herein. It was covered with a 6 percent w/v acetone solution of syndiotactic PVTFA according to the procedure of Example 2. After drying and in-situ reaction with ammonia vapor, this PVA shell melt-blown web was hydrophilic as demonstrated by spontaneous and nearly instant wetting with water. The resistance of this hydrophilic treatment to washout was demonstrated by 16 repeated soak/squeeze/dry cycles with pure water, resulting in a melt-blown web that was still as hydrophilic as it was initially, as shown by spontaneous and nearly instant wettability with water.

Example 20

A polypropylene woven fabric, obtained from the Arthur Kahn Co., of N.Y., N.Y., which was hydrophobic (i.e., a drop of water did not penetrate the fabric when it was placed on the fabric gently) was covered with a 4 percent w/v solution of syndiotactic PVTFA in acetone using the method of Example 2. (The weave of the starting fabric was coarse enough, however, to allow water to penetrate if any pressure was applied to the drop.) This resulted in a shell of PVTFA enveloping the surface of the fabric's fibers. Upon reaction of the PVTFA covered fabric with the ammonia vapor of ammonium hydroxide, as in Example 2, the fabric having a PVA shell about its surfaces became hydrophilic as demonstrated by spontaneous and nearly instant wetting with water.

Example 21

In order to show the availability of the hydroxyl functional groups of the hydrophilic shell towards chemical derivatization, the hydrophilic membrane from Example 1 was reacted with an acid chloride. Enough sebacyl chloride was added to a glass vessel to cover a piece of the vacuum dried membrane placed in the vessel. These were allowed to react for ½ hour at room temperature. The sample was rinsed in 1,1,1-trichloroethane to remove excess acid chloride. Infrared spectroscopy of the reacted membrane showed a new carbonyl absorption at $1737^{-1}$ cm and a decrease in the hydroxyl absorption at $3300^{-1}$ cm, which indicated that esterification of the hydroxyl group had occurred.

Example 22

A microporous polypropylene (PP) membrane, made by thermally induced phase separation as disclosed in U.S. Pat. No. 4,726,989 (Mrozinski), Example 9, having a Bubble Point maximum pore size of 0.65 μm, an average Gurley of 6.4 sec per 50 cc of air and a thickness of 0.82 mm was extrusion saturated with a 4.5 percent (w/v) solution of syndiotactic PVTFA according to procedure of Example 1 except that the membrane was dried for about 45 seconds. The resulting treated membrane had a PVTFA addon of 25.6 percent. A PVA shell membrane was prepared by hydrolyzing the PVTFA treated membrane in a stream of anhydrous ammonia according to the procedure of Example 9, followed by hydration with deionized water and drying at room temperature for about four (4) minutes. The PVA shell membrane had a Bubble Point pore size of 0.575 μm and was hydrophilic as demonstrated by it being spontaneously and nearly instantly wetted with water.

The filtration performance of the PVA shell membrane, the untreated PP microporous membrane and a commercially available microporous membrane, namely a 0.22 μm Durapore ™ polyvinylidene difluoride microporous membrane (available from Millipore Corp, Bedford, Mass.) were compared by measuring the turbidity of the filtrate obtained when each membrane was challenged with a submicron sized suspension. A Hach Ratio Turbidimeter (Model 18900), available from Hach Instruments (Fort Collins, Col.) was used to determine filtrate turbidity. The challenge suspension was prepared by adding six drops of a Fastek 0.22 μm sized latex sphere suspension (formerly available from Eastman Kodak) to 1600 ml of ultrapure water which had a turbidity of 0.08 Nephelometric Turbidity Units (NTU) to produce a suspension having a turbidity of 117 NTU. A 47 mm diameter disk of the test membrane was placed on the support plate of a Gelman Magnet Filter Holder, the top of the filter holder installed and the filter holder placed on a vacuum filtration flask. A laboratory vacuum of approximately 56 cm Hg was applied to the filter flask and the average time required to collect 100 ml of filtrate for each membrane filter and the turbidity of each filtrate sample as measured on the Hach Turbidimeter are reported in Table 10.

TABLE 10

| Membrane Sample | Time/100 ml Filtrate (seconds) | Turbidity (NTU) |
|---|---|---|
| PP Membrane | 90* | 1.62 |
| PVA Shell Membrane | 195 | 0.325 |
| Durapore Membrane | 155 | 5.4 |

There was no flow through the untreated membrane until it had been wet with isopropanol.

The data in Table 10 shows that the microporous membrane filter based on the PVA shell membrane of the present invention has significantly better particle retention properties than the untreated membrane as is evidenced by the lower turbidity of the filtrate obtained using the PVA shell membrane. Reasonably close filtration rates between the PVA shell membrane and the Durapore membrane implies that the two membranes have porosities which are quite similar but the lower turbidity of the filtrate obtained with the PVA shell membrane suggests that it is likely that the PVA shell membrane has either a smaller pore size or a higher tortuosity as compared to the Durapore membrane and consequently it can provide superior filtration performance.

Microporous membrane filters known to provide absolute control over bacterial contaminants above a critical size can be used to "cold pasteurize" or sterilize thermally sensitive aqueous fluids. Several techniques are used to validate the retentive efficiency, compatibility, and life expectancy of filters with an absolute pore-size rating above 0.02 μm. While a rigorous validation of filter efficiency requires the use of several techniques, an indication of filter efficiency can be provided by challenging the filter with 0.22 μm latex particle and comparing the concentration of spheres up- and downstream of the filter by means of turbidimetric analysis (see Goldsmith et. al., Pharmaceutical Manufacturing, Nov. 1985. pp 31–37). The data in Table 10 suggests that the PVA shell membranes of the present invention have the potential of realizing an "absolute" rating for control of particles larger than 0.22 μm and thus, might be suitable for sterilization of aqueous fluids.

Example 23

A standard acid copper plating tank having a capacity of 189 liters was filled with an aqueous electrolyte solution containing 210 g/L of copper sulfate, 60 g/L of sulfuric acid, 75 ppm of chloride ion, 0.4% (v/v) of "CuFlex" 327 liquid grain refining additive commercially available from McGean-Rohco, Inc. of Cleveland, Ohio, and 0.125% (v/v) "CuFlex" 326 liquid brightener additive also commercially available from McGean-Rohco, Inc. Temperature in the tank was maintained at 24° C. The cathode and anode were 15.24 cm squares of exposed copper with the reverse sides masked. The anode was covered by anode bags of the compositions shown in Table 11. The cathode and anode were spaced 10 cm. apart. Four volts DC was applied and the amperage was recorded as an indication of the efficiency of the anode bag to pass current. All of the anode bags were soaked in the electrolyte for 18 hours before the test.

TABLE 11

| Example | Bag material | $T_0$ Current Flow | $T_1$ min. Current Flow |
|---|---|---|---|
| 23A | 0.12mm PE(1) (hydrophobic) | None | None |
| 23B | 0.05mm PVA/PE(2) | 14.5 amps | 14.5 amps |
| 23C | PP fabric(3) | 13.5 amps | 13.5 amps |
| Control | None | 14.5 amps | 14.5 amps |

(1) This hydrophobic PE membrane was prepared according to Example 23 of U.S. Pat. No. 4,539,256.
(2) This example was prepared according to Example 1 above.
(3) This fabric is a polypropylene fabric outer surface with a napped interior, having a 12 oz/yd$^2$ sateen weave and a thread count of 64 × 38, commercially available as "Poly Nap" style 7020 anode bags from W. D. Forbes Co. of Minneapolis, MN.

Example 24

An anode bag was constructed from PVA shell PE membrane prepared according to Example 1 and having a Bubble Point Pore Size of 0.463 μm, a porosity of 73.6%, and a thickness of 0.06 mm was fitted over a titanium anode basket containing copper chips. A "Poly Nap" style 7020 anode bag was installed over the membrane anode bag for protection, even though the "Poly Nap" fabric anode bag reduced current flow. The anode assembly was installed in the tank and aqueous electrolyte solution used in Example 23 maintained at the same temperature. The tank also contained a filter with a polypropylene filter cartridge having a retention rating of 1 μm and a nominal length of 25 cm. Platings from this tank were very smooth and shiny, indicating the membrane anode bag maintained a clean solution. The filter cartridge remained unexpectedly clean, and the electroplating current flow rate was at or near the maximum, notwithstanding the presence of the "Poly Nap" fabric anode bag. Deterioration of the "CuFlex" 326 and 327 additives was significantly reduced; the replenishment rate for the additives was halved. After completion of the experiment, the anode bag assembly was removed. A significant quantity of sludge and residues were retained in the assembly, more than when the "Poly Nap" fabric anode bag had been used alone.

Example 25

A nickel electroplating tank similar to that illustrated in FIG. 7 was assembled, filled with an aqueous electrolyte solution containing 450 g/L of nickel sulfamate and 30 g/L of boric acid. Three different tests were run using the same components except for variation of the composition of the diaphragm separating the cathode and anode compartments.

In the first test, no diaphragm was used. In the second test, a 100% cotton denim cloth was used. In the third test, a PVA shell PE membrane was used. In each of the tests, the conductivity of the diaphragm was measured after the diaphragms were saturated in the electrolyte solution in the tank.

The following conditions were measured: the tank was maintained at 49° C. The aqueous electrolyte solution had a pH of 3.8 and a specific gravity of 1.35. The cathode having a 49 cm diameter rotated at 5 rpm. The diaphragm having a 60 cm diameter covered aperture separating the cathode and anode compartments.

The application of from 1 to 7 volts D.C. generated from about 10 to 80 amps for each test. There was no measurable difference among the conductivity of the PVA shell PE membrane, the cotton cloth, or no diaphragm at all.

With no diaphragm present, any debris present flowed freely during the agitation of the electrolyte between the cathode and the anode compartments. However, the PVA shell PE membrane had smaller pore sizes than the cotton cloth, efficiently reducing the amount of circulating debris without any measurable drop in electroplating current flow.

Example 26

Samples of a hydrophilic membrane prepared according to Example 1 were subjected to 14 day exposures to 36% $H_2SO_4$ and 30% KOH solutions to determine if the PVA shell would be subject to degradation under conditions typically encountered in electrochemical cells having an aqueous-based electrolyte. Results of the exposure study are reported in Table 12.

TABLE 12

| Hydrophilic Membrane Stability Studies | | | |
|---|---|---|---|
| Property | Initial | 36% $H_2SO_4$ Acid | 30% KOH Base |
| Gurley Permeability (sec/50cc) | 37.3 | 76 | 55 |
| Pore Size (Microns) | 0.353 | 0.30 | 0.339 |
| % Porosity | 70.16 | 63.3 | 64.1 |
| Tensile (MD) (psi) | 2487 | 2847 | 2653 |
| Tensile (TD) (psi) | 1029 | 1340 | 1216 |
| % Elongation (MD) | 67 | 107 | 90 |
| % Elongation (TD) | 185 | 170 | 110 |

After exposure to both the acid and alkaline soaks, the hydrophilicity of the membranes was comparable to that of the original membrane. No significant weight loss or dimensional shrinkage of the samples was noted.

Example 27

A sample of the hydrophilic membrane of Example 1 was subjected to a 14 day exposure to a 36% $H_2SO_4$ solution maintained at 49.5° C. to determine if the PVA shell would be subject to thermal or oxidative degradation under elevated temperature conditions which could be encountered in electrochemical cells having a hydrophilic electrolyte. The acid solution was placed in a modified Dewar condenser which was used to condense cyclopentane (B.P. 49.5° C.) to maintain a constant elevated temperature. Results of the exposure study are reported in Table 13.

TABLE 13

| Thermal and oxidative Stability Study | | |
|---|---|---|
| Property | Initial | 36% Sulfuric Acid |
| Gurley Permeability (sec/50 cc) | 53.4 | 37.7 |
| Pore Size (microns) | 0.365 | 0.384 |
| % Porosity | 65.6 | 63.6 |
| Tensile (MD) (psi) | 2609 | 2678 |

TABLE 13-continued

| Thermal and oxidative Stability Study | | |
|---|---|---|
| Property | Initial | 36% Sulfuric Acid |
| Tensile (TD) (psi) | 1752 | 1483 |
| % Elongation (TD) | 404 | 453 |
| % Elongation (TD) | 545 | 616 |

Examination of the data in Table 13 suggests that there is no significant degradation of the hydrophilic membrane under the elevated temperature conditions used in Example 26.

Example 28

A sample of the hydrophilic membrane of Example 1 (basis weight 0.022 gm/m$^2$) was thermally point bonded to a 10 gm/m$^2$ basis weight polyethylene microfiber web (made using Dow 6806 Polyethylene resin, available from Dow Chemical, Midland, Mich., in a procedure similar to that described in Wente, Van E., "Superfine Thermoplastic Fibers" in Industrial Engineering Chemistry, Vol. 48, pages 1342 et seq (1956) or in Report No. 4364 of the Naval Research Laboratories, published May 25, 1954 entitled "Manufacture of Superfine Organic Fibers" by Wente, Van E., Boone, C. D., and Fluharty, E. L.) in a regularly spaced dot pattern. The point bond areas accounted for approximately 15% of the total surface area of the hydrophilic semipermeable membrane and reduced the porosity of the membrane by 15%. The electrolyte resistivity and compressibility of the resulting laminate was compared to the resistivity and compressibility of a glass microfiber and a silica filled polyethylene battery separator material. Results of this comparison are reported in Table 14.

TABLE 14

| Electrolyte Resistivity and Compression Studies | | |
|---|---|---|
| Material | Electrolyte Resistivity (mohm in$^2$/20min) | % Compression |
| Hydrophilic Membrane Laminate | 15.7 | 31 |
| Silica Filled PE | 8-12 | Not Acceptable |

As shown in Table 14, the electrolyte resistivity and percent compression of the electrochemical cell separators based on the PVA shell membranes of the present invention are significantly superior to those demonstrated by the silica filled PE materials currently being used as electrochemical cell separators.

Example 29

Diffusion studies of mannitol through hydrophobic PE microporous membranes and hydrophobic PE microporous membranes rendered hydrophilic by a syndiotactic PVA shell were conducted to measure any difference in flux rates of water soluble mannitol (simulating therapeutic agents) therethrough. Radiolabeled 3H-mannitol was studied using standard diffusion cell methodology. A "Valia-Chien" side by side diffusion cell (as described in "Drug Development and Industrial Pharmacy" 1985 No. 11, pg. 1195, the disclosure of which is incorporated by reference, and commercially available from Crown Glass of Somerville, N.J.) was used with a PE membrane, prepared according to Example 23 of U.S. Pat. No. 4,539,256 (Shipman) and a PVA shell PE membrane, prepared according to Example 1 above. Each membrane was placed between the donor and receiving chambers of the diffusion cells. Three milliliters of Hepes Buffer at a pH of 7.0, was pipetted into each chamber and equilibrated to 32° C. At t=0, the radiolabeled 3H-mannitol samples (commercially available from NEN Research Products, a DuPont company, of Boston, Mass.) were added to the donor chamber. Aliquots were removed at hourly intervals and analyzed by standard liquid scintillation counting methods.

The permeability coefficient, P, was obtained through a plot of cumulative permeant in the receiver compartment per unit area per driving force vs. time. The expression which was plotted was:

$$P = \frac{(C_{r,t} * V_r) + SM_{r,t-1}}{(C_{d,t} - g_r/g_d * C_{r,t}) * A}$$

where $C_r$ is concentration in the receiver cell, t is time in hours, $V_r$ is volume in the receiver cell, $SM_r$ is the sum of the previously sampled mass in the receiver cell, $C_d$ is concentration in the donor cell, g is activity coefficient of 3H mannitol in an activity ratio between receiving and donor cell, and A is area of diffusion. $G_r/g_d$ was assumed to be 1.

The results showed a permeability coefficient of 0.0005 cm/hr for the hydrophobic PE microporous membrane. The permeability coefficient measured for the PVA shell PE microporous membrane was 1.856 cm/hr.

Example 30

The procedure of Example 29 was replicated, except that a 50:50 ethanol/water solution was used in the diffusion chamber in place of the Hepes Buffer when experimenting with the PE microporous membrane and water was used in the diffusion chamber in place of the HEPES Buffer when experimenting with the PVA shell PE microporous membrane. The average of 4 tests on each type of membrane are shown in Table 15.

TABLE 15

| Ex. | Membrane | Permeability Coeff. (cm/hr) | Gurley (sec) | Pore Size (μm) | Porosity |
|---|---|---|---|---|---|
| 30A | PE | 0.32 | 791 | 0.11 | 60 |
| 30B | PVA/PE | 2.55 | 20 | 0.68 | 72 |

Example 31

The procedure of Example 29 was replicated, except that a $H^3$-Mannitol was replaced with a 0.1M solution of Triprolidine HCl (commercially available from Burroughs-Welcome of Research Triangle Park, N.C.) in HEPES Buffer. The results showed a permeability coefficient of 0.0005 cm/hr for the hydrophobic PE microporous membrane. The permeability coefficient measured for the PVA shell PE microporous membrane was 0.9162 cm/hr.

Example 32

Two groups of samples of microporous PE membrane, prepared according to Example 23 of U.S. Pat. No. 4,539,256 were laminated to a transparent, 200 μm thick polyethylene terephthalate (PET) substrate sheet using a poly(vinylidene chloride)-based emulsion adhesive commercially available from Union Chemical of Schaumberg, Ill. as No. 5514.

One group of samples was rendered hydrophilic according to the procedure described in Example 2 above. The other group of samples remained hydrophobic.

All of the samples were about 19 μm thick, had a porosity of about 60%, and had an average pore size of about 0.2 μm in diameter.

A color image was attempted to be printed on both groups of samples using a Hewlett-Packard "PaintJet ™" printer using Hewlett-Packard "51606C" aqueous-based ink.

For the hydrophilic microporous PE membrane group of samples, the surface was receptive to the aqueous-based ink. An undistorted, crisp image was loaded in the porous membranes spontaneously and nearly instantly. After completion of loading of the images, about three minutes, the membranes could be touched by hand or other object without smearing the images.

By comparison, for the hydrophobic microporous PE membrane group of samples, the aqueous-based ink beaded-up on the outside of the porous surfaces and did not penetrate into the pores of the membranes. No ink could be loaded into the pores; the images on the surface of the membranes smeared upon contact whenever touched by hand or another object, even after two hours after application.

The images loaded in the hydrophilic microporous PE membrane group of samples were encapsulated by fusing the pores of the membrane. The fusing was accomplished by heating the membranes with a heat gun to a temperature of greater than about 132° C. The images remained undistorted and crisp in the locations where the ink had been loaded. The membranes were restructured into a transparent film. The laminates of transparent substrate and transparent film having the undistorted and permanent images were useful as an overhead transparencies when backlit. The images encapsulated in the laminates were unaffected by touching with hands and wiping with water.

Example 33

A sample of hydrophilic microporous PE membrane, laminated and prepared according to Example 32, was loaded with an image in the manner according to Example 32. To restructure the membrane and encapsulate the image, the imaged laminate was passed through a nip-roll. The nip-roll had a silicon upper roll and a lower metal roll inductively heated to about 136° C. The membrane having the image was fused without distorting the image. The laminate was useful as an overhead transparency having a protected, tamper resistant image encapsulated therein.

Example 34

A sample of hydrophobic microporous PE membrane laminated to PET in the manner according to Example 32 was loaded with an organic-based ink from a "Sharpie" felt-tipped permanent marking pen commercially available from Sanford Corporation of Bellwood, Ill. Rather than having the image bead-up on the surfaces as had occurred in Example 32, the organic-based ink was loaded into the pores of the hydrophobic membrane.

The image loaded in the hydrophobic membrane sample was encapsulated by fusing the pores of the membrane. The fusing was accomplished by heating the membrane with a heat gun in the manner according to Example 32. The image remained undistorted and crisp in the locations where the ink had been loaded. The membrane was restructured into a transparent film. The laminate of transparent substrate and transparent film having the undistorted and permanent image was useful as an overhead transparency when backlit. The image encapsulated in the laminate was unaffected by touching with hands and wiping with isopropanol, a solvent for this ink.

Example 35

A sample of hydrophilic microporous PE membrane was laminated to transparent PET and prepared according to Example 32. The image of a signature was loaded with aqueous-based ink into the pores of the membrane by handwriting. The image loaded in the hydrophobic membrane sample was encapsulated by fusing the pores of the membrane with a heat gun in the manner according to Example 32. The membrane was restructured into a transparent film. The laminate of transparent substrate and transparent film having an undistorted and permanent image was useful as a tamper-resistant document such as a security card or credit card. The image in the laminate is unaffected by touching with hands and wiping with water.

Example 36

A sample of the same hydrophobic microporous PE membrane as used in Example 32 was laminated to transparent PET in the manner according to Example 32. The image of a signature was loaded with an organic-based ink from a "Sharpie" felt-tipped permanent marking pen (commercially available from Sanford Corporation of Bellwood, Ill.) into the pores of the membrane by handwriting. The image loaded in the hydrophobic membrane sample was encapsulated by fusing the pores of the membrane with a heat gun in the manner according to Example 32. The membrane was restructured into a transparent film. The laminate of transparent substrate and transparent film having an undistorted and permanent image was useful as a tamper-resistant document such as a security card or credit card. The image in the laminate is unaffected by touching with hands and wiping with isopropanol, a solvent for this ink.

Example 37

A sample of the same hydrophobic microporous PE membrane as used in Example 32 laminated to a transparent polyester substrate in the manner according to Example 32, was rendered temporarily hydrophilic by using a 1% (w/w) solution of a surfactant, "Igepal CO-660" (having a HLB value of 13.2 and commercially available from GAF, Inc., of New York), in a 60/40 methanol/water solvent. The surfactant solution was coated on the porous surfaces of the hydrophobic membrane in the manner according to Example 1 of U.S. Pat. No. 4,501,793 (Sarada), the disclosure of which is incorporated by reference.

An image was loaded and encapsulated in the manner according to Example 32. The resulting transparent laminate having an undistorted and permanent image was useful as an overhead transparency.

Example 38

Two samples of the same hydrophobic microporous PE membrane as used in Example 32, laminated to a transparent polyester substrate in the manner according to Example 32, were rendered temporarily hydrophilic by using a 2% (w/v) solution of a non-ionic surfactant, "Tween-21" (having a HLB value of 13.3 and commercially available from ICI America of Wilmington, Del.) in a 50/50 ethanol/water solvent. The surfactant solution was coated on the porous surfaces of both hydrophobic membrane samples in the manner according to Example 1 of U.S. Pat. No. 4,501,793.

Both samples were loaded with aqueous-based ink according to Example 32.

The first sample was heated with a heat gun in the manner according to Example 32 within 30 minutes after the aqueous-based ink had been loaded. The second sample was heated in the same manner after 30 minutes after the aqueous-based ink had been loaded.

The first sample produced an undistorted and permanent image encapsulated and protected in the fused film, whereas the second sample produced a distorted image due to diffusion of the ink during the time between the loading and fusing.

Example 39

The experiments identified in Example 36 were repeated, except that a 2% (w/v) ethanol solution of amorphous poly(vinylpyrrolidone) (commercially available as "PVP K-90" from GAF Inc.) was used to coat the hydrophobic membrane to render the membrane temporarily hydrophilic.

As reported in Example 35, the first sample fused within 30 minutes of image loading produced an undistorted and permanent image, whereas the second sample fused after 30 minutes after loading produced a diffused image.

Example 40

A 0.05 mm thick hydrophobic microporous polyethylene membrane having 70 percent void volume prepared according to Example 23 of U.S. Pat. No. 4,539,256 and a second like membrane prepared according to the procedure of Example 1, were used as substrates. The unmodified polyethylene membranes were presoaked in acetone and then in pH 6.3 aqueous citrate buffer solution prior to coating to improve wetting characteristics. The hydrophilic microporous polyethylene membrane was used as received. The enzyme used was a special-grade, high-purity glucose oxidase powder (having a "Finnsugar stated activity" of 110 units/mg) from Finnsugar Biochemicals, Inc. of Schaumberg, Ill. Enzyme solutions were prepared using this powder and 0.1M, pH 6.3 citrate buffer of food-grade quality prepared using 27.9 g citric acid trisodium salt dihydrate, 0.98 g citric acid, and 1 liter of deionized water. Reagents for buffer preparation were obtained from Sigma Chemical Company of St. Louis, Mo.

Twelve membrane disks of 15.5 $cm^2$ apparent exterior surface area were saturated with 55 microliters of a 0.65 mg/ml glucose oxidase enzyme solution prepared in pH 6.3 citrate buffer. Thus, each disk was coated with approximately 0.04 mg of enzyme. The saturated disks were dried in a desiccator at room temperature and pressure for several hours prior to testing.

The enzyme solution did not wet out well on the disks prepared using the pre-wetted, hydrophobic, microporous polyethylene membrane.

Oxygen utilization rates were determined using a Model 5300 Biological Oxygen Monitor equipped with Model 5331 Standard Oxygen Probes and a constant temperature bath operating at 30° C. (Yellow Springs Instrument (YSI) Company, Inc., Scientific Division). The oxygen probes measure oxygen utilization in well-mixed, air saturated test solutions. For each test, 1000 microliters of a 30% w/v glucose solution were used as the substrate and an additional 2000 microliters of citrate buffer were included. The microporous membrane was tested in the air-saturated solution; small disks (20 mm$^2$) of membrane were attached to the stirrer in the oxygen monitor test vial. Since each test solution and membrane were well-mixed and in intimate contact, the oxygen utilization rate was assumed to be uniform throughout the test vial.

Four types of samples were tested using the YSI Biological Oxygen Monitor: blank solution; enzyme stock solution; enzyme-loaded, pre-wetted, hydrophobic, microporous polyethylene membrane, and enzyme-loaded, hydrophilic, microporous polyethylene membrane. Table 16 lists oxygen utilization rates for the samples. As anticipated, the blank solution did not exhibit any oxygen uptake and the enzyme stock solution exhibited a very high oxygen uptake. The enzyme-loaded hydrophobic microporous polyethylene membrane sample exhibited a lower oxygen uptake than the microporous polyethylene membrane.

TABLE 16

Oxygen Utilization Rates For Various Glucose Oxidase Enzyme-Loaded Microporous Polyethylene Membranes

| Sample Description | Oxygen Uptake ($\mu$l O$_2$/mg enzyme-hr) |
|---|---|
| Blank Solution | 0 |
| Stock Solution | 112,000 |
| (0.65 mg/ml glucose oxidase) | |
| Hydrophobic, Microporous Polyethylene Membrane (pre-wetted prior to coating) | 15,400 |
| Hydrophilic, Microporous Polyethylene Membrane: | |
| Sample 1 | 53,100 |
| Sample 2 | 35,700 |
| Sample 3 | 39,300 |
| Sample 4 | 35,800 |
| Sample 5 | 39,100 |
| Sample 6 | 54,700 |

Example 41

In order to demonstrate that the glucose oxidase-loaded, hydrophilic polyethylene membrane is effective in removing oxygen from the headspace of a container, the following product test was performed.

For each of twenty four samples, a 25 mm diameter glass vial having a polyethylene snap-cap and a height of 25 mm was filled using 12 ml of deionized water. This provided a headspace of approximately 4.5 cm$^3$ in the vial. The oxygen volume in this headspace was approximately 1 cm$^3$.

The inside surface of each snap-cap was coated with 0.1 ml of a gelatin solution of the following composition: 6.7 g "Knox TM" gelatin (available from Knox Gelatine Inc., Englewood Cliffs, N.J.), 154 g dextrose (available from Fisher Scientific, Inc.), and 225 ml deionized water. This quantity of solution provided a glucose concentration of 0.068 g of glucose.

To supply the enzyme for the reaction, 25 mm diameter disks of hydrophilic microporous polyethylene membrane prepared according to Example 1 were loaded with 50 $\mu$l of a solution containing 2.5 mg/ml glucose oxidase enzyme, 10 weight percent sucrose (available from Sigma Chemical Company), and pH 6.3 citrate buffer. This provided 0.125 mg glucose oxidase for the reaction. The loaded disks were placed on a polytetrafluoroethylene (PTFE) sheet and dried in a circulating air oven for 10 minutes at 45° C. The disks were then removed from the PTFE sheet and placed onto the gelatin-coated vial caps to which approximately 50 $\mu$l of pH 6.3 citrate buffer/10 weight percent sucrose solution had been added. All vials were sealed using the coated snap-caps prepared as described above.

Vials were stored in a refrigerator at 5° C. Vials were tested periodically to determine headspace oxygen content. These tests were performed using a MOCON/Toray LC700F Oxygen Headspace Analyzer available from Modern Controls, Inc., of Minneapolis, Minn. Oxygen content was found to decrease exponentially over a period of 1000 hours according to the equation y=19.7*e(−0.01x), where y is the oxygen content in the package headspace in percent and x is the time since sample preparation in hours.

Example 42

An experiment was performed to directly coat glucose and glucose oxidase enzyme solutions together onto hydrophilic microporous polyethylene membrane prepared according to the procedure of Example 1. The glucose solution was prepared using 500 g of dextrose, 1000 ml of pH 6.3 citrate buffer, and 2 g of granular potassium sorbate as a mold inhibitor (available from Monsanto Company, St. Louis, Mo.). The enzyme solution was prepared using 180 ml of pH 6.3 citrate buffer with an enzyme concentration of 2.5 mg/ml.

Each solution was placed in a separate three-necked, round-bottom flask with a base stopcock. The solutions were degassed using an aspirator and then back-flushed using nitrogen. The enzyme solution was fed into the flask containing the glucose solution. The two solutions were mixed.

Several milliliters of the mixed solution were coated onto hydrophilic microporous membrane using a glass bar. The membrane samples were dried in a forced-air oven for ten minutes at 90° F. The samples were then immediately placed in a polyethylene bag containing CaSO$_4$ desiccant available from W. A. Hammond Drierite Company, Xenia, Ohio.

Samples of 100 mm$^2$ dimension were cut from the coated membranes. These membranes were tested to determine activity using a YSI Biological Oxygen Monitor. The samples were tested in three milliliters of pH 6.3 citrate buffer at 30° C. approximately 72 hours after preparation. These membranes exhibited an average oxygen uptake of 0.175 cm$^3$/hr under the above test conditions.

Example 43

Glucose oxidase enzyme from Finnsugar Biochemicals, Inc. having a "Finnsugar stated activity" of 110 units/mg was added in a concentration of 2.5 mg/ml into a pH 6.3 citrate buffer aqueous solution containing 10% (w/v) sucrose. Hydrophilic membrane prepared according to Example 1 was saturated using rotogravure coating equipment. A 120P gravure roll was used on the coating equipment to load the enzyme system onto the hydrophilic microporous membrane's complex geometric configuration. The membrane was saturated with enzyme system because the citrate buffer aqueous solution wet the hydrophilic shell enveloping the porous membrane. The coating equipment was operated at a line speed of 4.6 m/min. and at a drying set-point temperature of 65° C. The dried, enzyme-loaded membranes were stored in a polyethylene bag containing CaSO$_4$ desiccant for two months prior to use, in order to simulate production storage times.

Independently, a nonwoven web of Nylon 6 commercially available from Allied Chemical under the brand "CFX Nylon 6" and having a basis weight of 53 g/m$^2$ was oriented and embossed at 175° C. This nonwoven web was coated with a 50% aqueous solution of glucose also containing 0.2 weight percent of potassium sorbate for preservative purposes. The coating die was a fluid-bearing die. The coating occurred at a line speed of 1.5 m/min. A drying temperature of 111° C. was used. A coating weight of 2.3 g of glucose/150 cm$^2$ was obtained.

The enzyme-loaded membrane and the glucose coated web were used in combination to form an absorbent pad for lunchmeat packaging. The meat packaged was 2.5 oz. "Carl Buddig Chicken" a smoked meat product commercially available from Carl Buddig and Company of Chicago, Ill. Both the enzyme-loaded membrane and the glucose coated web were cut into 10 cm $\times$ 12.5 cm pieces. The loaded membrane was placed on top of the coated web, with the enzyme-loaded membrane contacting the smoked chicken.

This combination was packaged in "Kapak" KSP410-1Mb barrier pouches commercially available from Kapak Corporation of Minneapolis, Minn. and cut to dimensions of 15 cm $\times$ 20 cm. The pouches had a 0.6 cm heat seal on three edges. The fourth edge was heat sealed using a "Sentinel TM" brand, bar-type heat-sealer commercially available from Packaging Industries Group, Inc. of Hyannis, Mass. The sealing conditions were 150° C. at a pressure of $4.1 \times 10^5$ Pa and one second exposure time.

The sealed lunchmeat pouches were then stored at 5° C., and oxygen content was monitored periodically over the next five days. Oxygen content was determined using an "LC-700F MOCON/Toray" oxygen headspace analyzer. Oxygen content was found to decrease exponentially over the five day period according to the equation: $y = 17.1 \ast e^{(-0.64x)}$, where y is the oxygen content in the package headspace in percent and x is the time since sample preparation in days. The headspace oxygen content decreased from about 21% upon heat sealing to approximately 3.5% on the third day to approximately 0.7% on the fifth day. By comparison, a smoked chicken package with the membrane prepared according to Example 1 above but without the enzyme-loaded therein retained about a 17% headspace oxygen content on the third day.

Neither the embodiments of the invention nor the examples described above limit the scope of this invention.

What is claimed is:

1. An article having a hydrophilic, polymeric shell, comprising:
   a supporting structure having a complex geometric configuration and surfaces about said structure and an extremely thin, self-interlocking, tactic, hydrophilic poly(vinyl alcohol) shell mechanically enveloping a multiplicity of internal and external surfaces while substantially retaining said complex geometric configuration, Wherein integrity of the shell mechanically enveloping said multiplicity of surfaces is imparted by the formation of tie molecules connecting two or more crystallites.

2. The article according to claim 1, wherein said supporting structure comprises polymeric, ceramic, cellulosic, glassy, metallic, or carbonaceous material; and
   wherein said supporting structure is a film, a membrane, a bead, a nonwoven web, a woven web, a spun thread, a porous fiber, or a porous hollow fiber.

3. The article according to claim 1, wherein said supporting structure comprises a polymeric composition; and
   wherein said polymeric composition comprises a polyolefin, a polyhalo-olefin, a polysulfone, a polyethersulfone, a poly dialkenyl phenylene oxide, a polyamide, a polyimide, a polyetherimide, a nylon, or combinations thereof.

4. The article according to claim 1, wherein said poly(vinyl alcohol) shell comprises from about an average of 10 to about an average of 4000 monolayers of poly(vinyl alcohol) enveloping said surfaces;
   wherein said poly(vinyl alcohol) shell is substantially insoluble in solvents having a solubility parameter differential to the solubility parameter of poly(vinyl alcohol) of greater than about 0.4;
   wherein said poly(vinyl alcohol) shell has a sufficient pore wetting surface energy to permit nearly instantly wetting of said article with water;
   wherein said tactic, hydrophilic poly(vinyl alcohol) shell has hydroxyl reactive sites available for further reaction;
   wherein said tactic, hydrophilic poly(vinyl alcohol) shell is formed in situ at at least a portion of said surfaces by a hydrolysis reaction of a hydrolysis reagent with a hydrophobic, polymeric poly(vinyl alcohol) precursor previously applied to said surfaces.

5. The article according to claim 4, wherein said precursor comprises a tactic homopolymer of vinyl trifluoroacetate, a tactic copolymer of vinyl trifluoroacetate monomer and a comonomer having a vinylic group therein, a tactic homopolymer of vinyl tert-butyl ether, or a tactic copolymer of vinyl tert-butyl ether monomer and a monomer having a vinylic group therein; and
   wherein said poly(vinyl alcohol) shell is the in situ reaction product of tactic polyvinyl trifluoroacetate and ammonia vapor, and wherein said poly(vinyl alcohol) comprises of from about an average of 10 to about an average of 4000 monolayers of tactic poly(vinyl alcohol) about said surfaces of said supporting structure.

6. The article according to claim 1, wherein regio-specific surfaces of said article are hydrophilic and regio-specific surface of said article are hydrophobic.

7. A method for the preparation of a hydrophilic, polymeric shell about an article having a complex geometric configuration comprising:
   (a) applying a tactic, hydrophobic, polymeric polyvinyl alcohol precursor to at least a portion of surfaces of the article; and
   (b) reacting said polymeric precursor with a hydrolysis reagent in situ on a multiplicity of internal and external surfaces to form an extremely thin, self-interlocking, tactic, hydrophilic poly(vinyl alcohol) shell mechanically enveloping said surfaces while substantially retaining the complex geometric configuration.

8. The method according to claim 7, wherein said applying step comprises wiping, dipping, rolling, knifing, or extruding;

wherein said precursor is in a solvent which wets said surfaces and solubilizes said precursor in a concentration less than about 15 weight percent; and wherein said precursor comprises a tactic homopolymer of vinyl trifluoroacetate, a tactic copolymer of vinyl trifluoroacetate monomer and a comonomer having a vinylic group therein, a tactic homopolymer of vinyl tert-butyl ether, or a tactic copolymer of vinyl tert-butyl ether monomer and a monomer having a vinylic group therein.

9. The method according to claim 8, wherein the weight percent of said precursor in a solvent may be adjusted relative to pore sizes of surfaces of the article to control alteration of said complex geometric configuration.

10. The method according to claim 8, wherein at least a portion of said shell enveloping said surfaces is exposed to a temperature greater than a glass transition temperature of said shell to render hydrophobic regiospecific surfaces of the article.

11. The method according to claim 9, wherein said hydrolysis reagent has a pH greater than about 7.0;

wherein said hydrolysis reagent is a liquid, solution, or vapor which does not solvate said precursor;

wherein said hydrolysis reagent comprises sodium hydroxide, sodium carbonate, ammonium hydroxide, potassium hydroxide, ammonia vapor, or ammonia vapor with water or moisture vapor.

12. An article having a hydrophilic, polymeric shell, comprising:

a hydrophobic supporting structure having a complex geometric configuration and surfaces about said structure and an extremely thin, self-interlocking, tactic, hydrophilic poly(vinyl alcohol) shell mechanically enveloping said surfaces to render the article hydrophilic, without chemical crosslinking of poly(vinyl alcohol) within the shell and without chemical grafting of poly(vinyl alcohol) to said surfaces, while substantially retaining said complex geometric configuration of said supporting structure.

13. The article according to claim 12, wherein said hydrophobic supporting structure comprises polymeric, ceramic, cellulosic, glassy, metallic, or carbonaceous material.

14. The article according to claim 12, wherein said hydrophobic supporting structure is a film, a membrane, a bead, a nonwoven web, a woven web, a spun thread, a porous fiber, or a porous hollow fiber.

15. The article according to claim 12, wherein said hydrophobic supporting structure comprises a polymeric composition; and wherein said polymeric composition comprises a polyolefin, a polyhalo-olefin, a polysulfone, a polyethersulfone, a poly dialkenyl phenylene oxide, a polyamide, a polyimide, a polyetherimide, a nylon, or combinations thereof.

16. The article according to claim 12, wherein said poly(vinyl alcohol) shell comprises from about an average of 10 to about an average of 4000 monolayers of poly(vinyl alcohol) enveloping said surfaces.

17. The article according to claim 12, wherein said poly(vinyl alcohol) shell is substantially insoluble in solvents having a solubility parameter differential to the solubility parameter of poly(vinyl alcohol) of greater than about 0.4.

18. The article according to claim 12, wherein said poly(vinyl alcohol) shell has a sufficient pore wetting surface energy to permit nearly instantly wetting of said article with water.

19. The article according to claim 12, wherein said tactic, hydrophilic poly(vinyl alcohol) shell has hydroxyl reactive sites available for further reaction.

20. The article according to claim 12, wherein said tactic, hydrophilic poly(vinyl alcohol) shell is formed in situ at said surfaces by a hydrolysis reaction of a hydrolysis reagent with a hydrophobic, polymeric poly(vinyl alcohol) precursor previously applied to said surfaces.

21. The article according to claim 20, wherein said precursor comprises a tactic homopolymer of vinyl trifluoroacetate, a tactic copolymer of vinyl trifluoroacetate monomer and a comonomer having a vinylic group therein, a tactic homopolymer of vinyl tert-butyl ether, or a tactic copolymer of vinyl tert-butyl ether monomer and a monomer having a vinylic group therein.

22. The article according to claim 20, wherein said poly(vinyl alcohol) shell is the in situ reaction product of tactic polyvinyl trifluoroacetate and ammonia vapor, and wherein said poly(vinyl alcohol) comprises of from about an average of 10 to about an average of 4000 monolayers of tactic poly(vinyl alcohol) about said surfaces of said supporting structure.

23. A method for the preparation of a hydrophilic, polymeric shell about a hydrophobic article having a complex geometric configuration comprising:

(a) applying a tactic, hydrophobic, polymeric polyvinyl alcohol precursor to surfaces of the hydrophobic article; and (b) reacting said polymeric precursor with a hydrolysis reagent in situ on a multiplicity of internal and external surfaces to form an extremely thin, self-interlocking, tactic, hydrophilic poly(vinyl alcohol) shell mechanically enveloping said surfaces to render the hydrophobic article hydrophilic while substantially retaining the complex geometric configuration.

24. The method according to claim 23, wherein said applying step comprises wiping, dipping, rolling, knifing, or extruding.

25. The method according to claim 23, wherein said precursor is in a solvent which wets said surfaces and solubilizes said precursor in a concentration less than about 15 weight percent 26. The method according to claim 25, wherein the weight percent of said precursor in a solvent may be adjusted relative to pore sizes of surfaces of the article to control alteration of said complex geometric configuration.

27. The method according to claim 23, wherein said precursor comprises a tactic homopolymer of vinyl trifluoroacetate, a tactic copolymer of vinyl trifluoroacetate monomer and a comonomer having a vinylic group therein, a tactic homopolymer of vinyl tert-butyl ether, or a tactic copolymer of vinyl tert-butyl ether monomer and a monomer having a vinylic group therein.

28. The method according to claim 23, wherein said hydrolysis reagent has a pH greater than about 7.0.

29. The method according to claim 28, wherein said hydrolysis reagent is a liquid, solution, or vapor which does not solvate said precursor.

30. The method according to claim 29, wherein said hydrolysis reagent comprises sodium hydroxide, sodium carbonate, ammonium hydroxide, potassium hydroxide, ammonia vapor, or ammonia vapor with water or moisture vapor.

* * * * *